United States Patent [19]

Shofner et al.

[11] Patent Number: 5,544,090
[45] Date of Patent: Aug. 6, 1996

[54] REMOVAL OF UNDESIRABLE ENTITIES IN THIN WEBS OF TEXTILE MATERIALS

[75] Inventors: Frederick M. Shofner; Joseph C. Baldwin, both of Knoxville; Gordon F. Williams, Norris; Mark G. Townes, Knoxville, all of Tenn.

[73] Assignee: Zellweger Uster, Inc., Knoxville, Tenn.

[21] Appl. No.: 336,827

[22] Filed: Nov. 9, 1994

Related U.S. Application Data

[62] Division of Ser. No. 999,007, Dec. 31, 1992, Pat. No. 5,383,135.

[51] Int. Cl.⁶ ................................................. G01N 21/84
[52] U.S. Cl. ................ 364/552; 364/470.14; 364/470.01; 356/430; 356/431
[58] Field of Search ........................... 364/552, 470, 364/555–559, 468, 469; 356/430, 431

[56] References Cited

U.S. PATENT DOCUMENTS

| | | | |
|---|---|---|---|
| 3,851,972 | 12/1974 | Smith et al. | 356/72 |
| 4,417,149 | 11/1983 | Takeuchi et al. | 250/563 |
| 4,528,455 | 7/1985 | Loose | 250/563 |
| 4,766,324 | 8/1988 | Saadat et al. | 250/563 |
| 4,801,809 | 1/1989 | Burk et al. | 250/559 |
| 4,879,471 | 11/1989 | Dahlquist | 250/359 |
| 4,909,930 | 3/1990 | Cole | 209/564 |
| 4,988,875 | 1/1991 | Ortiz et al. | 250/330 |
| 5,087,120 | 2/1992 | Anthony | 356/36 |
| 5,095,214 | 3/1992 | Eder | 250/563 |
| 5,127,726 | 7/1992 | Moran | 356/237 |
| 5,130,559 | 7/1992 | Leifeld et al. | 250/562 |

FOREIGN PATENT DOCUMENTS 545129  9/1993  European Pat. Off. .

*Primary Examiner*—Ellis B. Ramirez
*Assistant Examiner*—Craig Steven Miller
*Attorney, Agent, or Firm*—Luedeka, Neely & Graham, P.C.

[57] ABSTRACT

An apparatus and method for monitoring and processing a web of textile materials which includes a plurality of entities including fibers, neps, seed coat fragments and trash. The web is monitored, preferably by an imaging unit, to produce a monitor signal. A computer receives the monitor signal and locates the position of entities of interest and controls a web processor in accordance with the location of the entities. Preferably, the web processor includes ejectors for ejecting entities from the web under the control of the computer. In one embodiment, the web is formed by a sampler and forming apparatus which removes a sample of fibers from a supply and reconfigures it into a desired configuration, such as a web, for being monitored.

9 Claims, 21 Drawing Sheets

Dimensions are in inches.

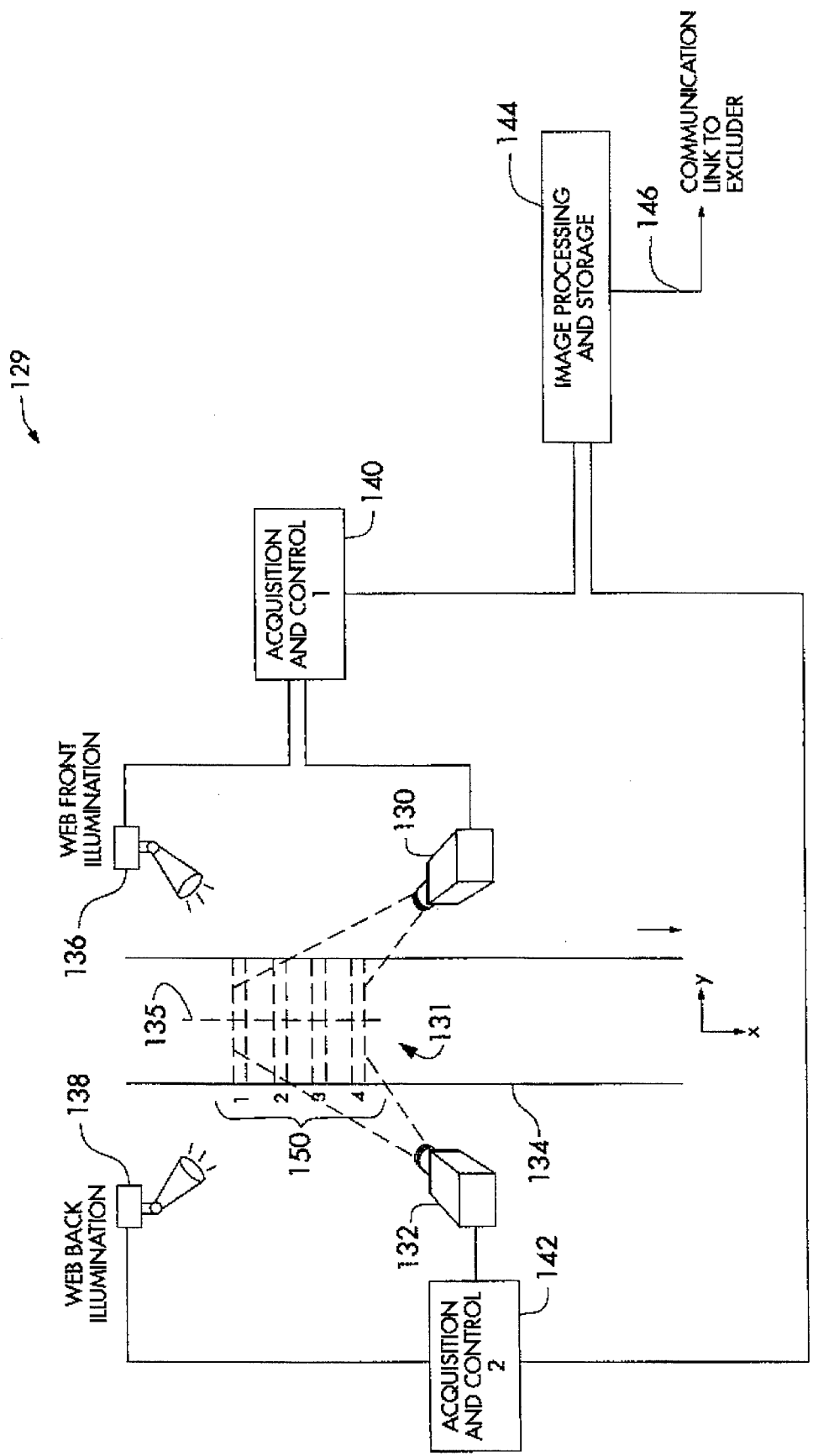

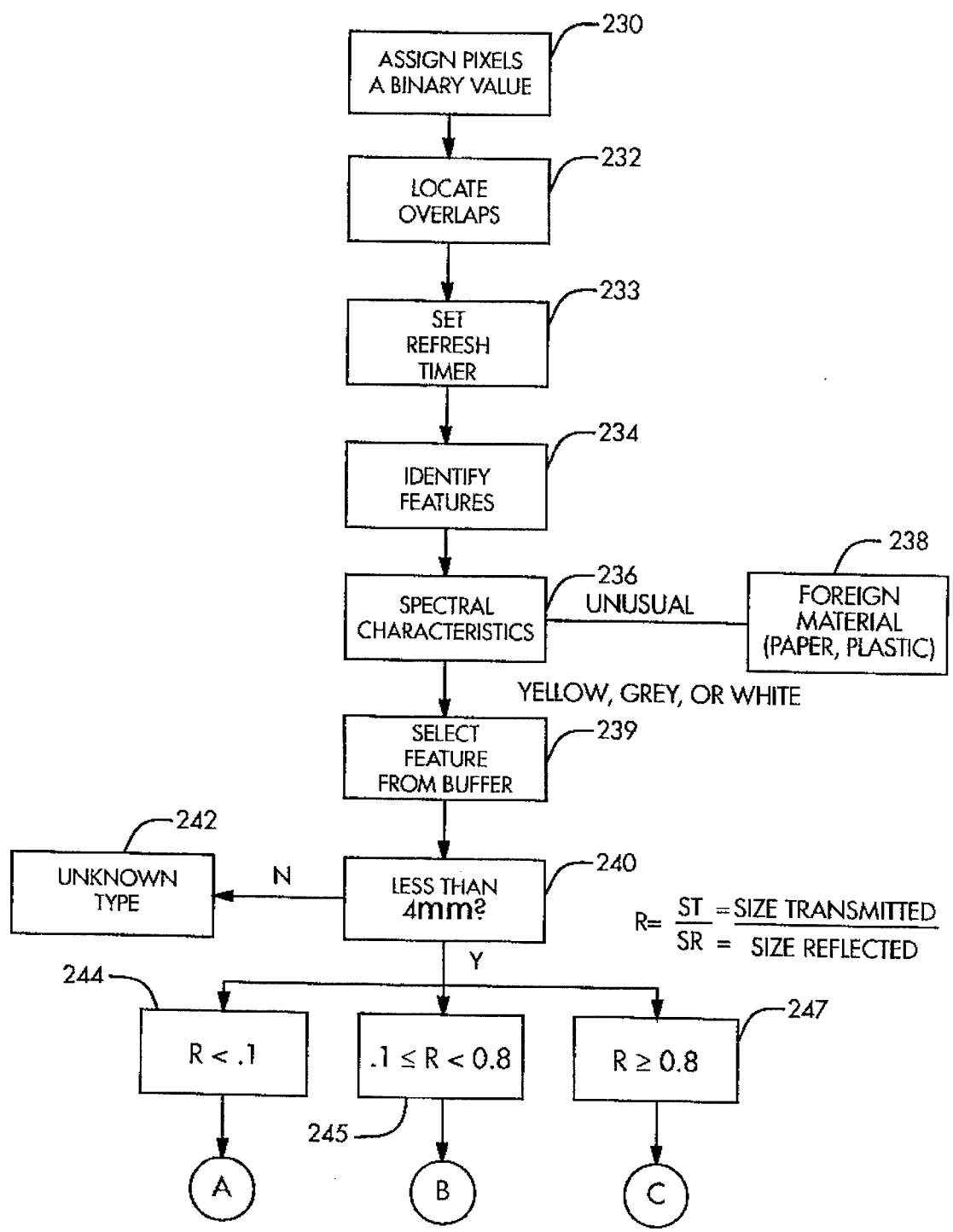

REMOVAL OF UNDESIRABLE ENTITIES IN THIN WEBS OF TEXTILE MATERIALS

This is a division of application Ser. No. 07/999,007, filed Dec. 31, 1992 now U.S. Pat. No. 5,383,135.

FIELD OF THE INVENTION

The present invention relates to methods and apparatus for the in-process, real-time measurement and control of entities in thin webs of textile materials. In the preferred embodiment, such entities include single fibers, single neps, and single trash particles in cotton and other fibrous materials. The thin webs are either intentionally formed from a sample of material acquired from the process or inherently found within certain processing machines. Preferred measurement is by image analysis preferably based on charge-coupled device (CCD) cameras with extended spectral response.

To further define the field of this invention, means are provided for acquisition of in-process samples from continuously-operating textile manufacturing process machinery. Image analysis then enables spatial, spectral, and temporal pattern recognition or filtering (SSTF). SSTF in turn enables identification of individual entities in the thin webs. Finally, this invention discloses utilization of control signals derived from SSTF for the purposes of removing undesirable entities from thin webs or of directly controlling the quality characteristics of thin webs of textile materials in textile processing machinery.

BACKGROUND OF THE INVENTION

The presence of undesirable entities in textile materials such as neps and trash particles is a problem whose severity is generally increasing. Production and harvesting techniques of cotton, for example, demand more aggressive cleaning action at the gin or in the early stages of processing in the textile mill. These actions remove foreign matter or trash but in many cases break the trash into smaller particles and leave some of it in the fibrous mass. This makes it more difficult to remove in later stages. Worse, this increasingly aggressive cleaning action generally increases the level of nep formation. It is therefore increasingly important to monitor the levels of these undesirable entities on a continuous basis in the gin or mill in order to optimally control them; one must measure before one can control.

In most production environments it is completely impossible to monitor 100% of the process throughput and samples of in-process material must be acquired for measurement. In textile processing machines the fiber states available for sampling are in tuft form or in sliver. New means are therefore needed to acquire a representative sample and prepare it into thin web format for image analysis measurement. There are notable exceptions where judicious application of recently-developed image analysis technology enable 100% monitoring of the process throughput. A good example, as will be disclosed below in a preferred embodiment, is monitoring the thin web of a carding machine. Prior art methods and apparatus result in overwhelmingly expensive or otherwise impractical applications of image analysis. Our invention overcomes the difficulties.

SUMMARY OF THE INVENTION

In accordance with the present invention, on-line monitoring is provided for controlling the quality of card web. Undesirable entities are Found in preferably 100% of the thin card web, Identified as to the severity of their impact upon subsequent processes or ultimately on sale price of the textile product derived therefrom, and then prioritized control action is taken to remove or exclude these entities from the web. These web-cleaning provisions are identified by the acronym "FIX".

In accordance with a particular aspect of the present invention, an apparatus is provided for monitoring and processing a web of textile materials, such as cotton being processed in a textile mill. The web includes a plurality of entities such as cotton fibers, neps, leaf trash, seed coat fragments, and other foreign matter. The web is monitored by an optical imaging unit, such as a video camera, and a monitor signal is produced containing information corresponding to the content of the web, including the location of entities in the web. A computer receives the monitor signal and determines the position of the entities based on the location information and generates control signals based on the determined positions. Web processing means receives the control signals and processes the web in response thereto for reducing the amount of entities contained in the web.

Preferably, the web processor includes ejectors positioned downstream of the imaging unit for selectively ejecting entities from the web. The computer is operable to determine when one or more entities are positioned for being ejected by the ejector and issuing an eject command in response to the entities being so positioned and the ejectors respond to the eject commands for ejecting entities from the web. The preferred ejectors include a row of nozzles positioned in a side-by-side relationship downstream of the monitor extending across the web. Pressurized air is supplied to the nozzles by fast-acting pneumatic valves under the control of the computer. When the monitor identifies an entity to be ejected, the computer determines when the entity will pass under the nozzles and which nozzle it will pass under. Then, the computer will issue a command to the fast-acting valves causing them to release air to the appropriate nozzle and blast the entity from the web with air.

In accordance with a particular embodiment of the present invention, an apparatus is provided for monitoring and processing a supply of textile materials being processed in a textile mill, in which the supply includes a plurality of entities including undesirable entities. A sampler and sample forming apparatus removes samples of fibers from the supply and forms the sample into a desired configuration and further delivers the reconfigured sample to a monitoring location. A monitor views the reconfigured sample of materials at the monitoring location and produces a monitor signal containing information corresponding to the content of the reconfigured sample. The monitor signals are provided to a computer that analyzes the entity content of the reconfigured sample and generates output signals based on the analyzed entity content including information as to undesirable entities contained within the reconfigured sample.

Preferably, the sampler and sample forming apparatus includes a needle sampler including a plurality of needles for engaging and holding entities in the supply of textile materials. A release mechanism selectively releases the entities from the needle sampler in a metered manner to release the entities at a selected rate of release. The released entities are received on a movable surface moving at a selected speed and thereby forms the entities into a desired configuration on the surface to thereby form the reconfigured sample on the moveable surface. The monitor views the reconfigured sample on the moveable surface.

The monitor of the preferred embodiment includes a video camera for viewing the web and a speed detector for detecting the speed of the web and producing a speed signal. Utilizing the monitor signal and the speed signal, the computer calculates the location of entities of interest relative to a web processor. Specifically, the computer determines the time at which one or more undesirable entities will be positioned at the web processor based on the location information contained in the monitor signal and the speed of the web. When undesirable entities are positioned at the web processor, they are processed under the control of the computer.

BRIEF DESCRIPTION OF THE DRAWINGS

The present invention may best be understood by reference to the following Detailed Description of preferred embodiments when considered in conjunction with the drawings in which:

FIG. 8 shows a block diagram of an optical imaging system including two CCD cameras and front and back illumination of a web;

FIGS. 17A and 17B constitute a flow chart illustrating the operation of a computer program illustrating one method for using the optical system of the present invention for distinguishing between different entities in a textile web;

DETAILED DESCRIPTION OF A PREFERRED EMBODIMENT

Web Forming Sampler

Figure 1:
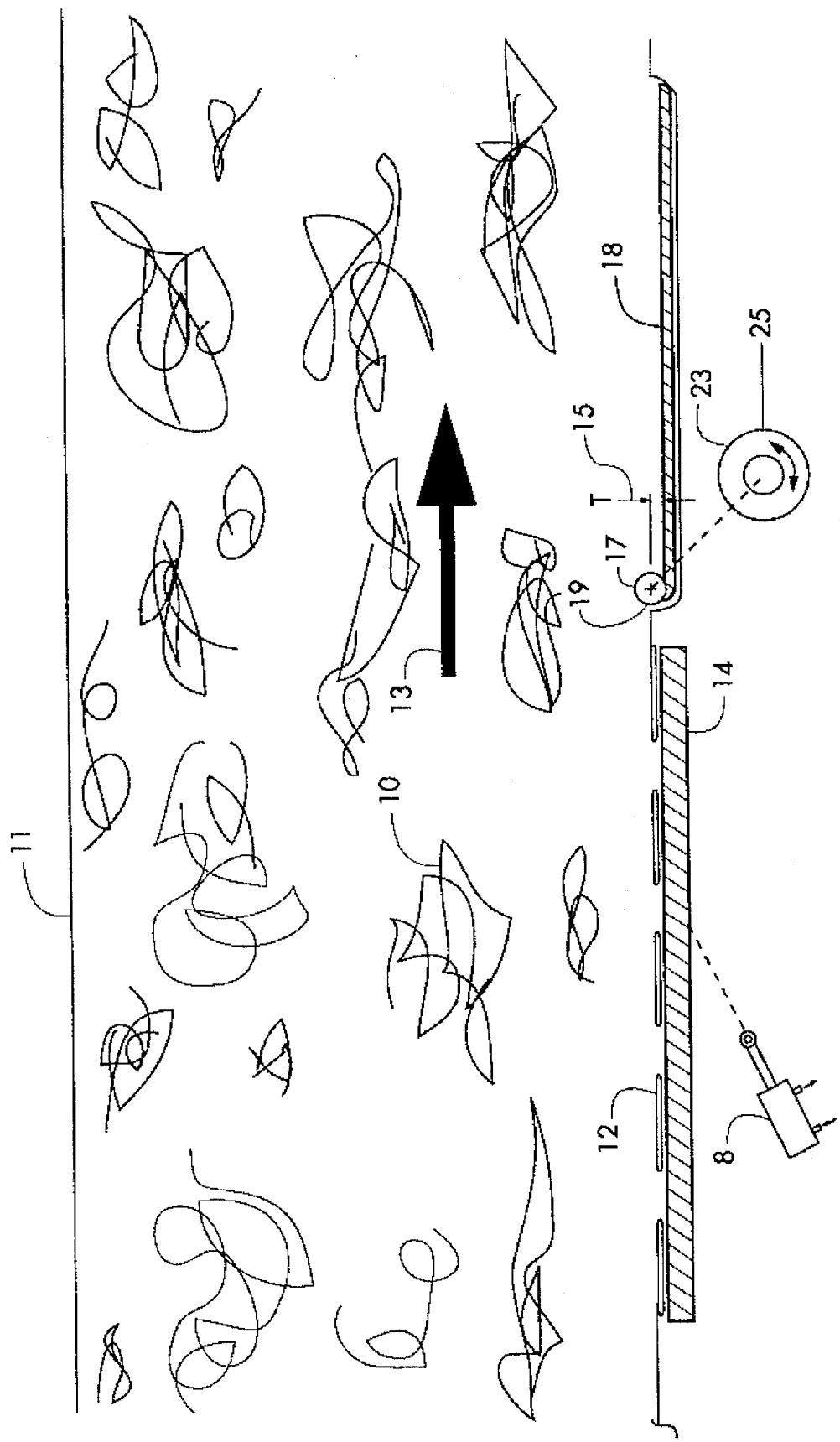
FIG. 1 is a somewhat diagrammatical cross-sectional view of tufts of fibers being transported pneumatically within a duct and showing a sampler in a wall of the duct.
Figure 2:
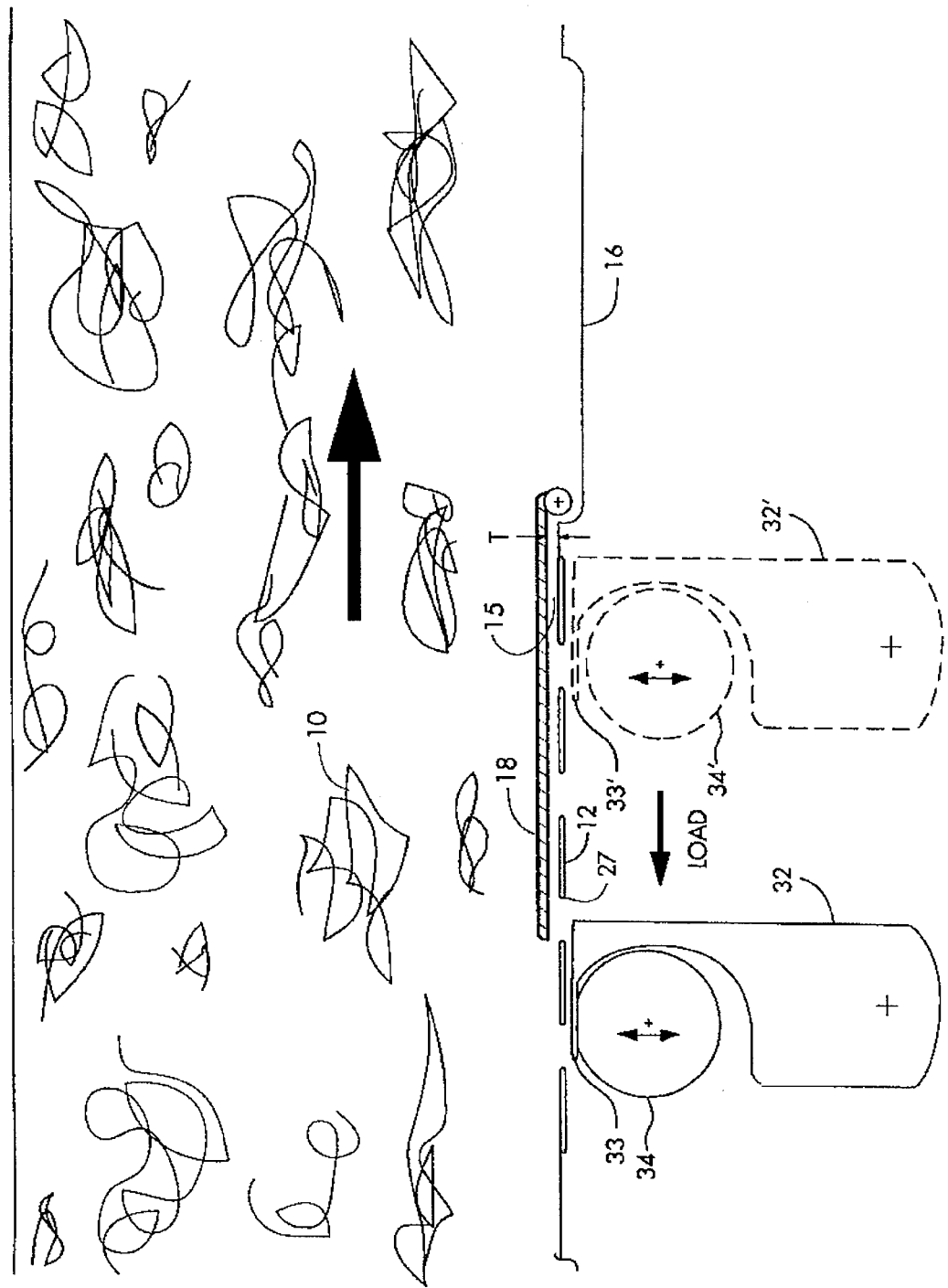
FIG. 2 is an illustration similar to FIG. 1 showing a sampler in operation removing samples of fiber from the duct.

FIG. 1 illustrates tufts of fiber 10 being transported pneumatically within a duct 11 in a direction indicated by arrow 13. On one side of the duct there is placed a perforated wall 12 in combination with a solid cover plate 14 to seal against the perforated wall and against the solid sides of the duct 11. Cover plate 14 is shown displaced from the perforated wall 12 for clarity but it is normally in air-tight contact with the duct 11 and perforated plate surfaces. This cover plate 14 overcomes pressure differentials between the inside and outside of the duct 11. Sampler plate 18, shown in stowed position in FIG. 1, is mounted on a drive shaft 17, which is actuated by means such as a pneumatic or hydraulic motor 23 and control system, and is rotated about an axis 19 upon command from a control signal on line 25 into the flow, thus capturing tufts 10 which are impacted upon it. In the course of rotating counter-clockwise into the flow, impacted tufts 10 of suitable amount corresponding to thickness T (15) in FIGS. 1 or 2, are collected and ultimately moved into a closed position by the rotary motion of the plate 18, as shown in FIG. 2. After plate 18 moves to the closed position shown in FIG. 2, the sealing plate 14 is moved perpendicularly to the plane of the drawing by a suitable mechanical mechanism such as a cylinder 8 and associated control system, to expose the perforated wall 12.

FIG. 2 illustrates that the sampling plate 18 has come to a closed or sampling position over the perforated plate 12. The sealing plate 14 has been retracted since the combined action of the fiber sample 20 on the perforated plate 12 and the sealing action of the sampling plate can withstand the pressure differential between the inside and outside of the duct 11.

As a result of this action, a fiber sample 20 is presented through the perforated plate holes 27 for sampling by a needle sampler 32, which needle sampler is one of three that is further described in co-pending Shofner et al. application entitled "Needle-Based Apparatus for Individualizing Fibers and Other Textile Entities For Testing Purposes," Ser. No. 07/999,305 filed Dec. 31, 1992 now U.S. Pat. No. 5,367,747. In the right-hand side of the lower part of FIG. 2 there is shown, in broken line format, a needle sampler 32' with the clamping/feed roll 34' in the retracted or open position. The needle sampler 32' (broken line) is just beginning its right to left motion. The row of needles 33', whose width into the paper is preferably about 2 to 4 inches, but which can be as short as one inch or as long as 6 inches or longer if needed, moves in close proximity to the perforated plate 12 and thereby acquires representative samples of entities 10 from the perforated holes 27 until the sampler 32 has been loaded and moved fully to the left. At this point the needle sampler 32 clamping/feed roll 34 is closed, as shown in solid lines in the lower left side of FIG. 2, and the sample loading step has been completed. In this figure the roll 34 is intended to represent a clamping feed roll that rotates around its center axis or moves linearly in response to rotate or translate control signals. The feed roll is preferable constructed of elastomer material.

The sampler 32 is carried by a suitable mechanism for translating it horizontally and rotating it downwardly. Further mechanisms, also well known in the art, enable the rotary and translational motion of the elastomer feed roll.

Figure 3:
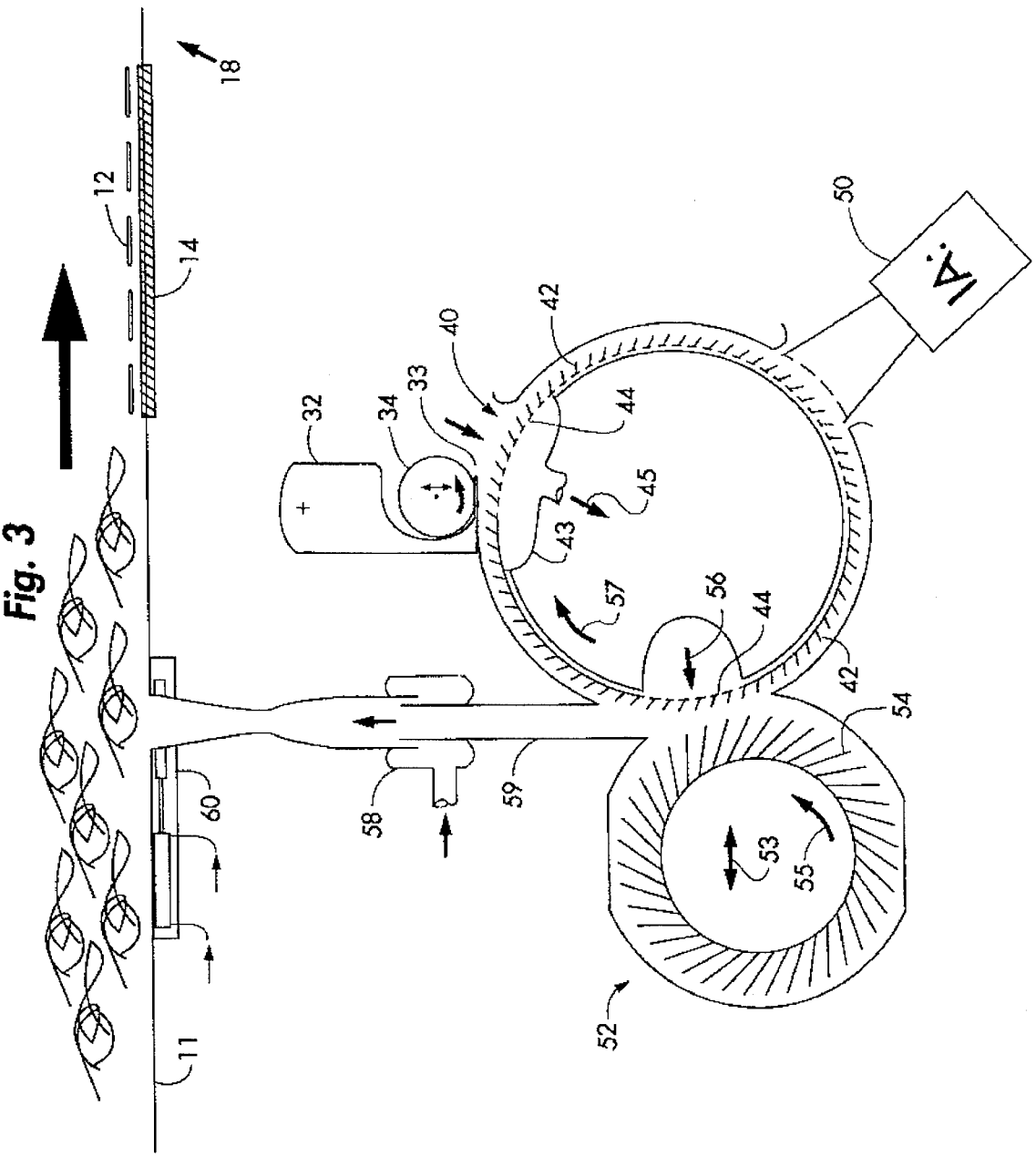
FIG. 3 is a somewhat diagrammatical drawing further illustrating the operation of the sampler and showing the sampler delivering fibers to a cylinder.

As shown in FIG. 3, the needle sampler 32 has been rotated and translated away from the sampling position which is adjacent to the perforated plate 12. The sealing plate 14 is moved back into a closed position as shown in FIG. 1 and the sampling plate 18 is rotated clockwise back into its stow position. The fibers which were captured on sampling plate 18 are blown away by compressed air (top and bottom, to clear the region) and re-injected into the pneumatic conveying air in duct 11. FIG. 3 further illustrates that the needle sampler has been rotated into registration with presentation cylinder 40. Cylinder 40, which preferably includes pins 42 on perforations 44 in its surface, combs and aligns the fibers and serves as a presentation device for the thin web of fibers and other entities deposited thereupon. (The thin web is not shown.) Fibers are uniformly released from the pins 33 by rotating the clamping/feed roll 34 in the fiber sampler 32 in concert with rotation of the thin web presentation cylinder 40 so that fibers and other entities are approximately uniformly deposited onto the cylinder 40. A plenum 43 and suction 45 on the plenum provide an air flow through perforations 44 to assist the deposition of entities from sampler 32 onto cylinder 40.

Figure 5:
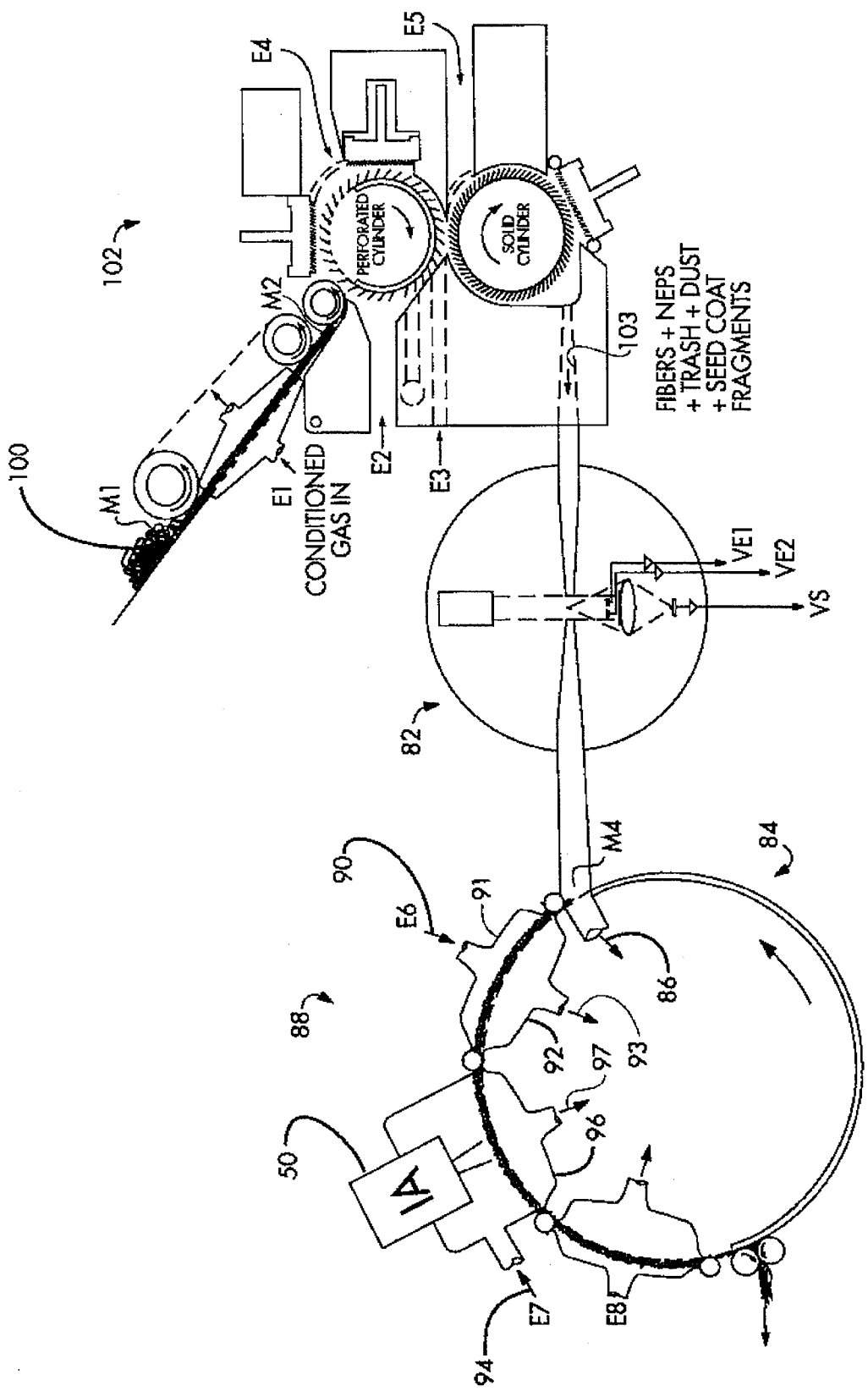
FIG. 5 illustrates another embodiment of the present invention in which textile fibers are processed by a fiber individualizer, transported through an individual fiber monitor, and deposited on a cylindrical screen for further monitoring.

In some applications, the pins 42 are excluded and the fibers and other entities are deposited on a fine mesh screen 84, similar to that shown in FIG. 5. The first objective of this transfer step is to transfer 100% of the fiber sample, including all entities in the sample such as neps or trash, without substantial modification, such as breakage. The second objective is forming the sample into the thin web format desired for presentation to the image analysis system 50. Further details of needle sampler 32, alternative needle sampling means, and alternative measurement means are disclosed in co-pending applications recited above and are incorporated herein by reference. Preferably, approximately 1 gram of sample is transferred from each needle sampler 32 to the presentation cylinder 40. This quantity is associated with a needle sampler 32 width of approximately 3 inches.

Presentation cylinder 40 is also about 3 inches in width and 6 inches in diameter. Its speed of rotation is set by the image analysis means 50 but speed is normally about 100 RPM. The presentation cylinder 40 presents a thin web of entities for examination by image analysis means 50. In the embodiment of FIG. 3, fine pins 42 and perforations 44 on cylinder 40 are used to assure uniform removal and loading as well as to assure some combing and separation actions of the sample as it is removed from the needles 33. The image analysis means 50 thus examine a thin web which has been deposited in a preferred manner. Consideration is given to uniformity and orientation of fibrous entities in the material sample as will be fully disclosed hereinafter.

Before explaining the image analysis or control dimensions of this invention, completion of the sampling cycle is explained. Upon completion of the image analysis measurement by means 50, the brush 52 in FIG. 3 is moved to the right as indicated by arrows 53 such that the bristles 54 engage the pins 42. The brush 52 and the presentation cylinder 40 are rotated as shown by arrows 55 and 57 whereupon the fibers, neps, trash, and other entities are removed from the presentation cylinder 40 by the combined action by the brush 52 and compressed air 56 applied through the perforated holes 44. A coaxial eductor 58 is used to supply suction through conduit 59 with which to drive airflow from the brush 52 and presentation cylinder 40 region back into the pneumatic conveying process duct 11. Upon completion of this action, slide valve 60 closes. The system is now prepared for another measurement sequence. In the above description, mechanical movements and control are accomplished by conventional means and preferably the entire operation is under control of a conventional microprocessor based controller or a computer, such as the computer system 144 of FIG. 8, but each step may be manually controlled, if desired.

Figure 4:
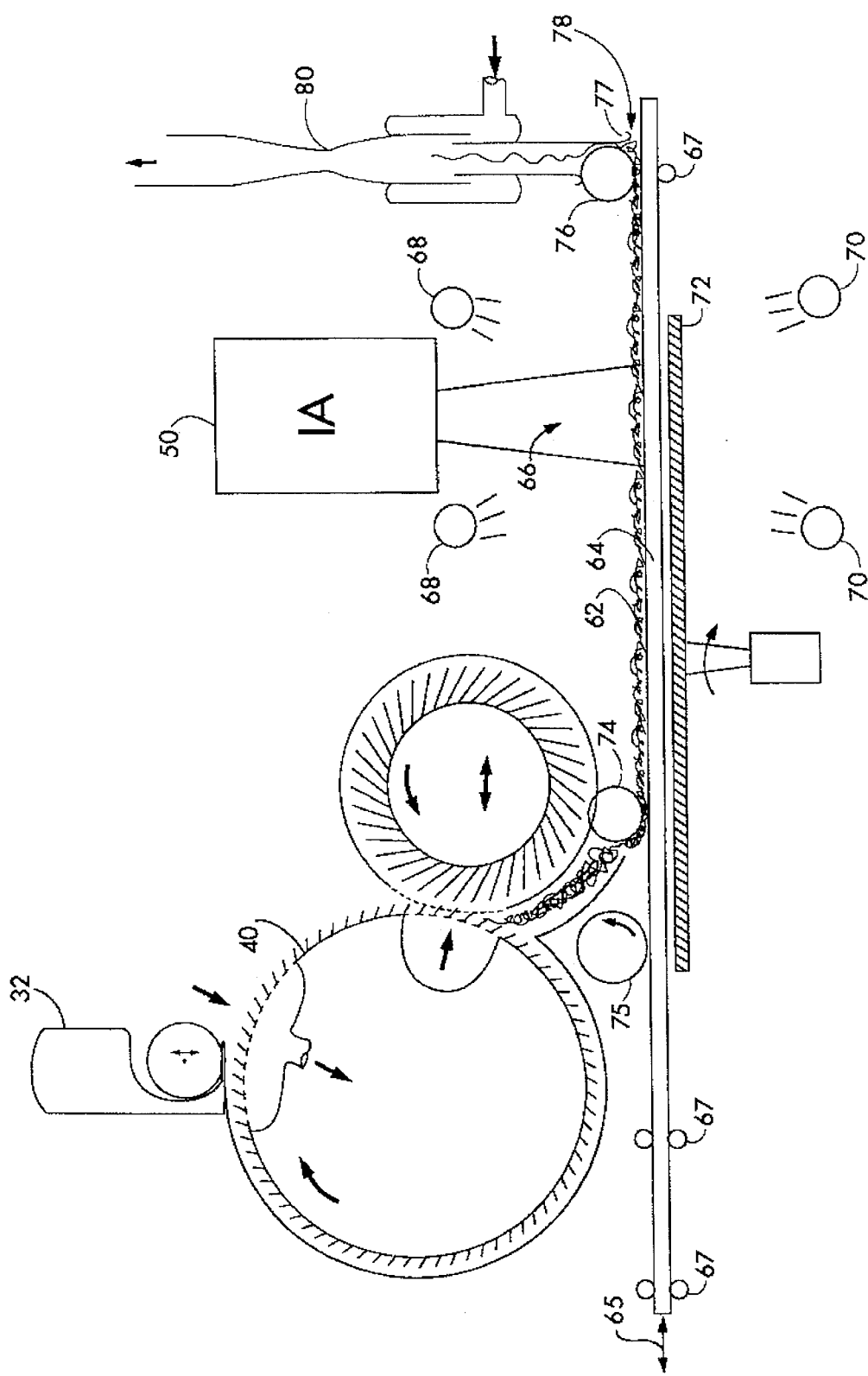
FIG. 4 is a drawing showing the sampler delivering fiber samples to a cylinder which, in turn, delivers the sample to a glass plate.

FIG. 4 reveals another embodiment utilizing substantially the same needle sampler 32 and image analyzer measurement means 50. A thin web 62 is formed for presentation to the image analysis system 50. In this case the sample is acquired by needle sampler 32 and spread on the presentation cylinder 40 as before, but in this case the thin web 62 is brushed off onto a glass plate 64 whose length is slightly greater than the circumference of the presentation cylinder 40. The plate 64 is mounted for left and right linear motion as indicated by arrows 65 and its frame (not shown) is driven by drive rolls 67. In this manner the density, orientation and other preparation and presentation features and effects on the sample by the cylinder 40 are retained, but a preferred viewing environment 66 is provided. In this environment front lighting 68, and back lighting 70 may be used together or separately for preferred illumination. Background contrast and other elements are represented by the motor driven element carrier 72. The carrier 72 preferably provides a black background, but it also may represent white or other colors, a mirror surface, or no element at all, for the back lighting mode. A wide variety of backgrounds with front illumination could be chosen to enhance contrast or resolution or, in general, the ability to recognize entity patterns.

Upon completion of measurement the thin web sample 62 moves with the glass plate 64 under guide roll 76 and is removed by clean compressed air from purge source 77 and carried out by an entrained air sweep 78 driven by coaxial eductor 80. The tested material is thus returned to the process as in FIG. 3. Cleaner wheel 75 removes residue and prepares the plate 64 for the next test.

FIG. 5 shows a fiber individualizing apparatus 102 supplying individual fibers and entities through a conduit to a sensing station 82 that in turn supplies the entities and fibers to a viewing station 88. The sample is individualized by apparatus 102. The individualized entities 103, after passing through electro-optical sensing station 82, are deposited on a rotating perforated drum 84. The deposition is aided by collection of the transport air by suction 86. At station 88 the image analysis system 50 is shown in similar fashion as in FIGS. 3 and 4. In this embodiment the sample has been conditioned with environmentally controlled gas 90 introduced at plenum 91 and discharged into a collection plenum 92 that is evacuated by suction 93. Also, the sample can be further conditioned by environmentally controlled air 94 which is similarly collected by plenum 96 and suction 97.

See DIRECT CONTROL OF FIBER TESTING OR PROCESSING PERFORMANCE PARAMETERS BY APPLICATION OF CONTROLLED, CONDITIONED GAS FLOWS, Ser. No. 07/999,226 co-filed Dec. 31, 1992, now U.S. Pat. No. 5,361,450, with the instant application.

It is evident that the peripheral speed of perforated cylinder 84 can be adjusted in combination with the sample 100 feed rate into the fiber individualizer 102 so that essentially individual entities are presented for inspection both by the electro-optical sensor 82 and by the image analysis system 50. Slower speeds of the presentation cylinder 84 enable multiple entities to be deposited and inspected by the image analysis system 50 at station 88. It can be appreciated that the time stamping concept introduced in co-pending application Ser. No. 07/762,613, filed Sep. 19, 1991, now U.S. Pat. No. 5,394,480, may be applied between the signals from the electro-optical light scattering sensor 82 and the image analysis system 50 at station 88. That is, there is a fixed time delay between when the sample 100 is sensed at station 82 and at station 88. Thus, the measurements from stations 82 and 88 may be time correlated.

Figure 6:
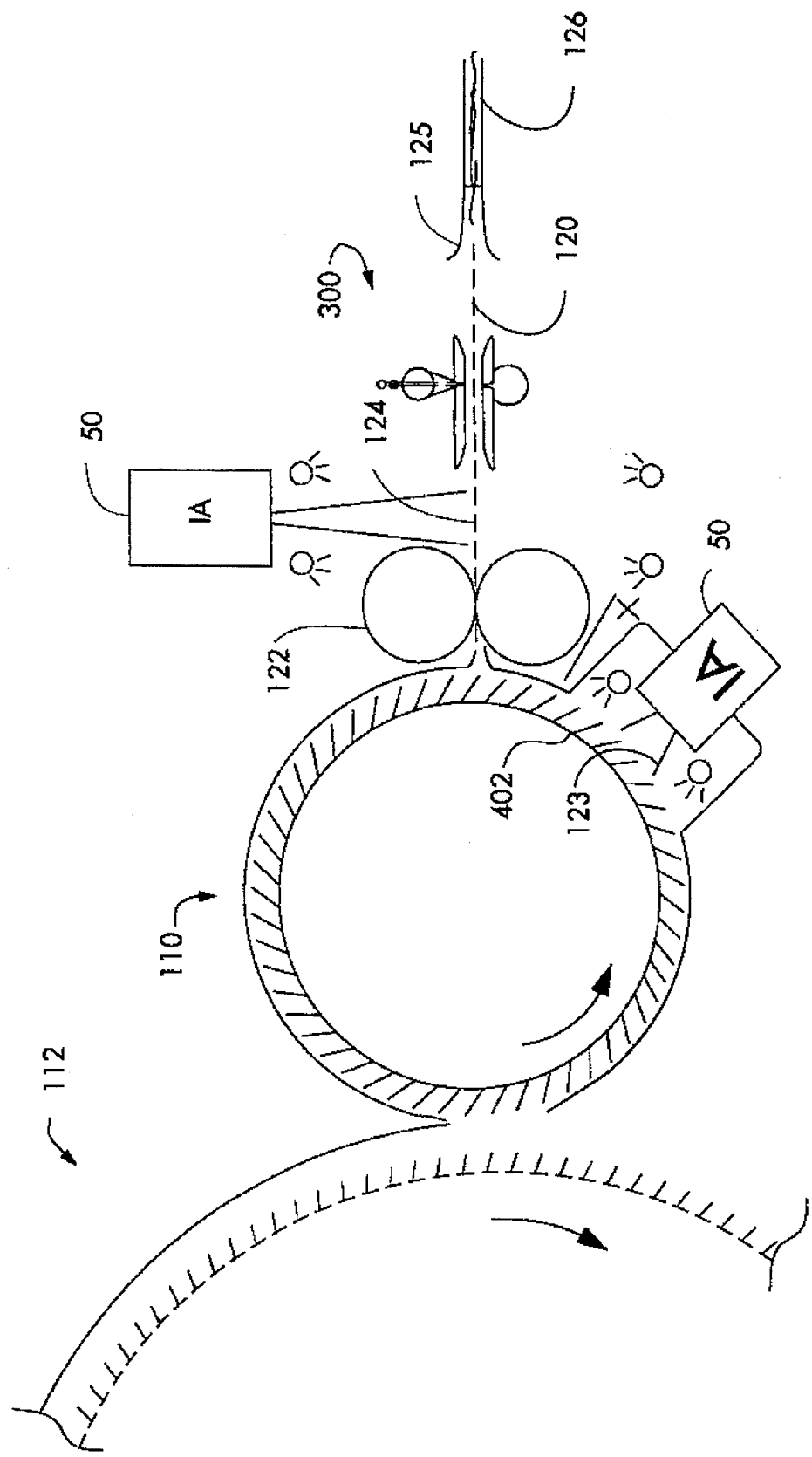
FIG. 6 is a cross-sectional view illustrating an implementation of the present invention in conjunction with a web on a doffer cylinder and/or a web as it leaves the doff rolls of a textile machine.

FIG. 6 reveals a most important embodiment for on-line process monitoring wherein image analysis means 50 inspect the thin web on a doffer cylinder 110 of a carding machine 112. Alternatively, image analysis means 50 inspect the web 120 as it exits the doff or crush rolls 122 and before it proceeds through a trumpet 125 and becomes a sliver 126. It will be readily understood that the entities, in terms of orientation and density are essentially the same on the doffing cylinder 110 as in the web 120. It will also be appreciated that the relative advantages of inspecting the web in "free" space 124, where front lighting and back lighting are much more readily achieved, is preferable for the highest contrast and resolution. However, in some cases it is not feasible to measure the web at space 124 as indicated in FIG. 6. In other cases the discrimination abilities of the image analysis system 50 are entirely adequate when examining the thin web as it is transported by the teeth on the doffer cylinder 110.

Figure 7B:
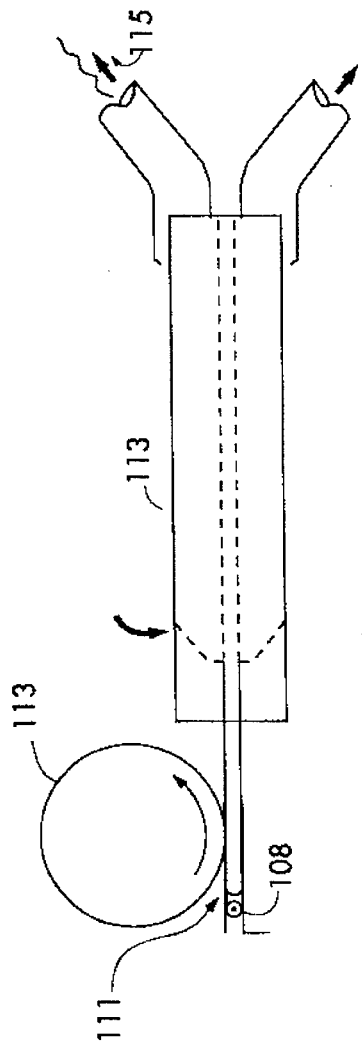
FIG. 7B is a schematic diagram of a processing station where fiber samples are removed from the needle sampler of FIG. 7A.
Figure 7A:
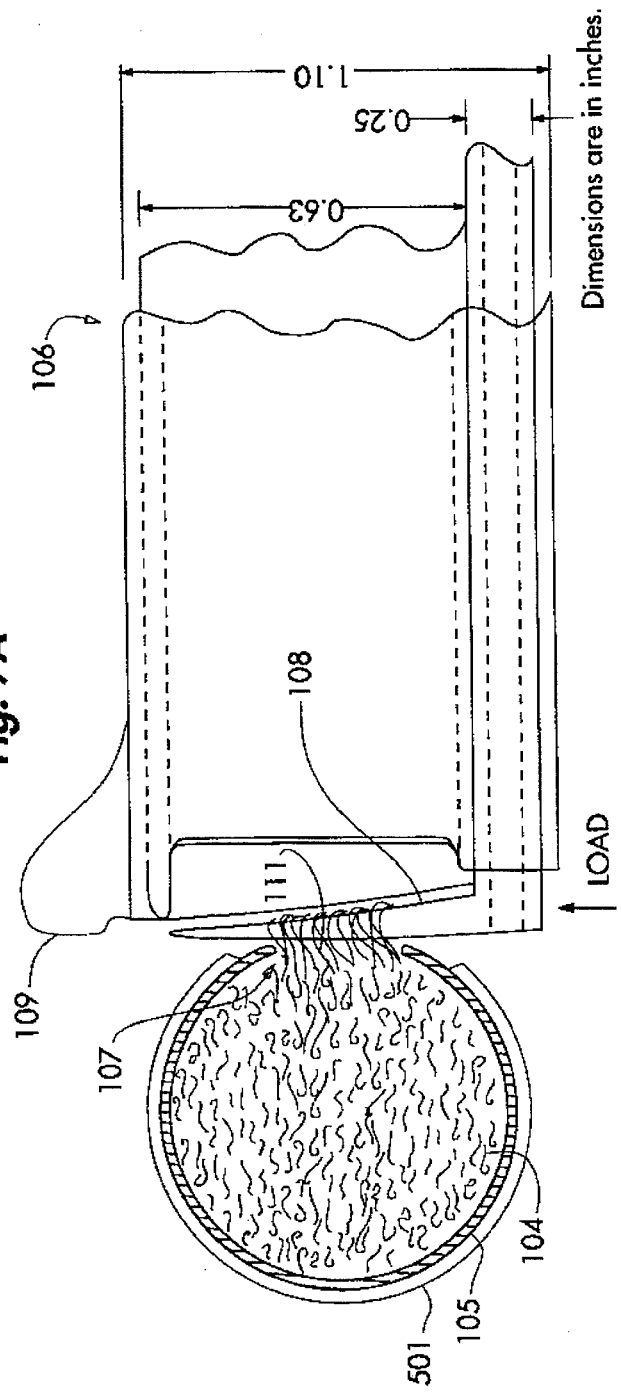
FIG. 7A is a somewhat diagrammatical cross-sectional view of a tube containing a sliver of textile fibers being sampled by a needle sampler.

FIG. 7A shows a cross-sectional view of a conduit 105 in which a sliver is transported. This conduit may be trumpet 125 seen in FIG. 6 or it may be any conduit through which sliver 126 is drawn. The trumpet collects the thin web 120 whose width is about one meter, into a sliver form, whose ultimate minimum diameter of about 1 cm and whose linear density is about 5 gm/m. Sliver 126 thus consists of fibers whose lengths are generally parallel to the transport direction. The dots 104 in the sliver transporting conduit 105 represent fiber cross sections. It is desirable to sample fibers and other entities in the sliver state, particularly where it is moving at perhaps 150 meters/min and FIG. 7A discloses our means therefor. The single needle sampler 106 in FIG. 7A is described in co-pending application entitled "Needle-Based Apparatus for Individualizing Fibers and Other Textile Entities for Testing Purposes," Ser. No. 07/999,305 filed Dec. 31 1992. Operation is as follows: Concentric cover housing 501 moves to expose holes 107 (single perforation). Sampler 106, with needle 108 and guide 109 set for sampling, is moved past hole 107 and a sample 111 of fibers and other entities is collected as explained for the multiple needle sampler above and in the reference above. The needle is closed and the sampler is transported to the next station.

At the next station, shown in FIG. 7B, the sample is further processed and prepared for testing. The sample 111 consists of about 1000–2000 fibers and associated other entities. The cover housing 113 is pulled away from the needle, the needle 108 is opened, and the elastomer feedroll 113 introduces the sample into an air flow 115. The sample may then be deposited on screen 84 in FIG. 5 for measurement by image analyzer means 50 or to other measurement means, including the AFIS system 102.

FIGS. 3, 4, 5, 6, 7A, and 7B thus disclose means by which thin webs may be formed from samples of textile material for the preferred examination by image analysis means. The samples may be automatically acquired from an operating process, may be part of a test sample for a laboratory quality control instrument, or may be inherently found already as thin webs in carding machines or the like. All may be advantageously examined with our preferred image analysis means 50. We now turn to the image analysis subject and disclose the concept of spatial, spectral and temporal pattern recognition or filtering, SSTF.

Image Acquisition System

Referring now to FIG. 8, there is shown an overview of the optical imaging system 129 which includes first and second optical imaging units 130 and 132, which include CCD cameras and appropriate optics explained below. Each of the imaging units 130 and 132 is positioned to view at least a 0.5 meter wide section of a web 134 which is preferably a web of non-woven textile fibers such as cotton. Only one camera or image analysis system is required for the moving web on the presentation cylinder 40 in FIG. 3, the viewing plate 64 of FIG. 4 or the mapping screen 84 of FIG. 5. These are test instrument applications and, among other features, the web properties, especially speed, can be adjusted to match image analysis system requirements. Contrariwise, for 100% web monitoring in a production machine, the image analysis system must accommodate the machine. The preferred embodiment now described is for monitoring card web in FIG. 6, either on the doffer cylinder 123 or after the crush rolls 122 in viewing position 124. For either location 123 or 124, two cameras are advantageous. Preferably, the imaging units 130 and 132 are positioned to view approximately one-half of the web with an overlap 135 of approximately 0.01 meter. The purpose of two imaging units 130 and 132 is to provide 100% optical viewing of the web, but reduce the data rate by approximately one-half. That is, by analyzing the data from each optical unit 130 or 132 separately, the data rate is approximately one-half that which would be required if a single unit was viewing the entire web and the single camera was obtaining the same resolution as two imaging units. Further, two cameras greatly relax requirements on lenses and other optical elements.

The moving web 134 is illuminated by broad band radiation sources 136 and 138 which provide both visible and non-visible light, including infrared. Source 136 illuminates the front of web 134 and when possible, as at 124 in FIG. 6, source 138 illuminates the opposite side, the back or lower side of web 134. With this illumination arrangement, the type of illumination impinging on the web 134 can be varied to provide information as to the amount of light transmitted through the web 134 from its back side or reflected from its front side, or both.

The imaging units 130 and 132 and the illumination sources 136 and 138 are connected through data acquisition and control units 140 and 142 to an image processing and storage computer system 144. The optical imaging units 130 and 132 produce image signals that are transmitted through the units 140 and 142 to the system 144 for processing, and the computer system 144 also issues control commands through the units 140 and 142 to the illumination sources 136 and 138 and, thereby, controls the intensity and duration of the illumination on the web 134. The system 144 also includes an information link 146 that provides information and control to an excluder system that is hereinafter described.

Operation of the Image Acquisition System

Figure 9:
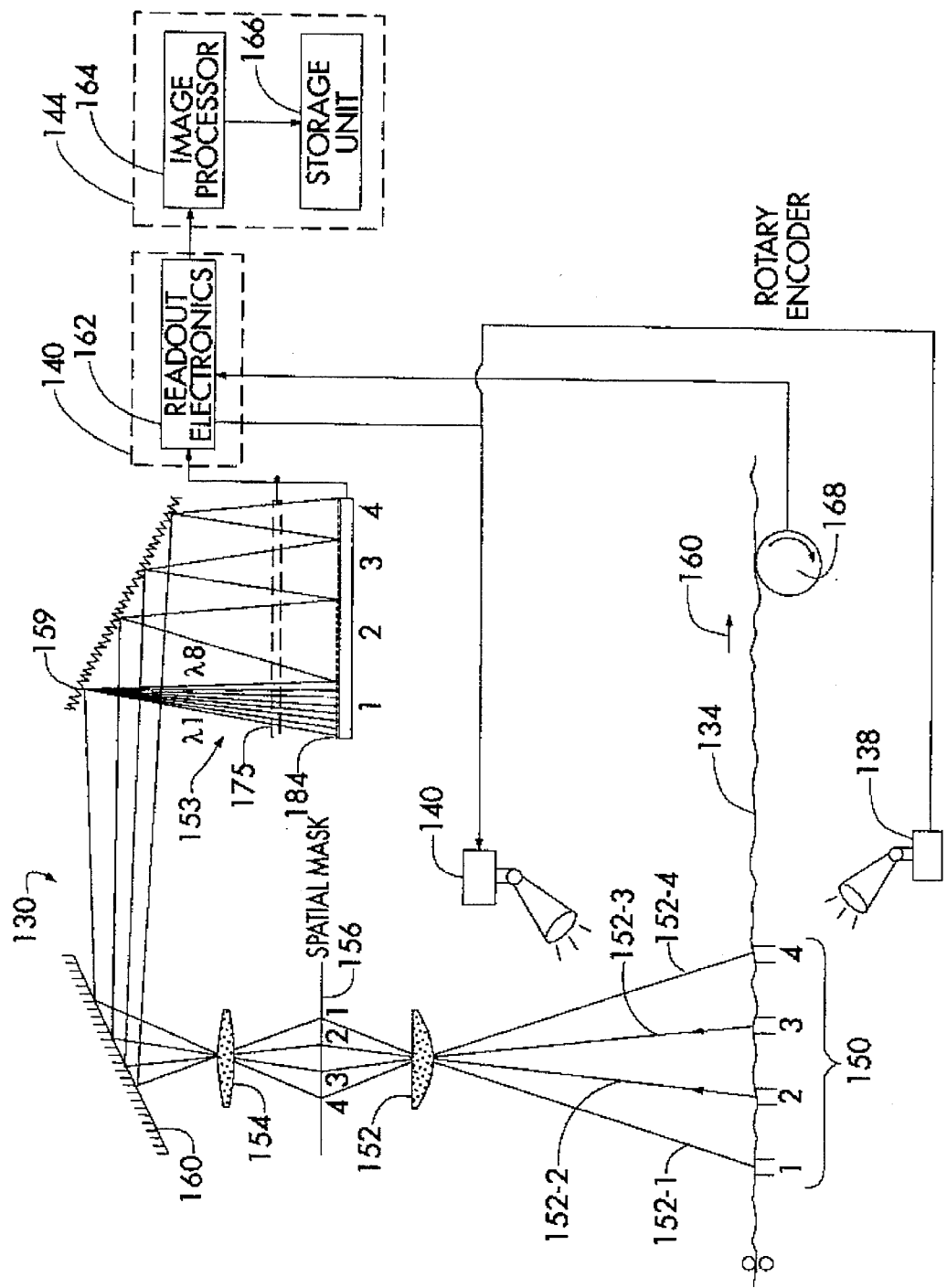
FIG. 9 is a more detailed schematic diagram of the optical imaging system of FIG. 8.
Figure 10:
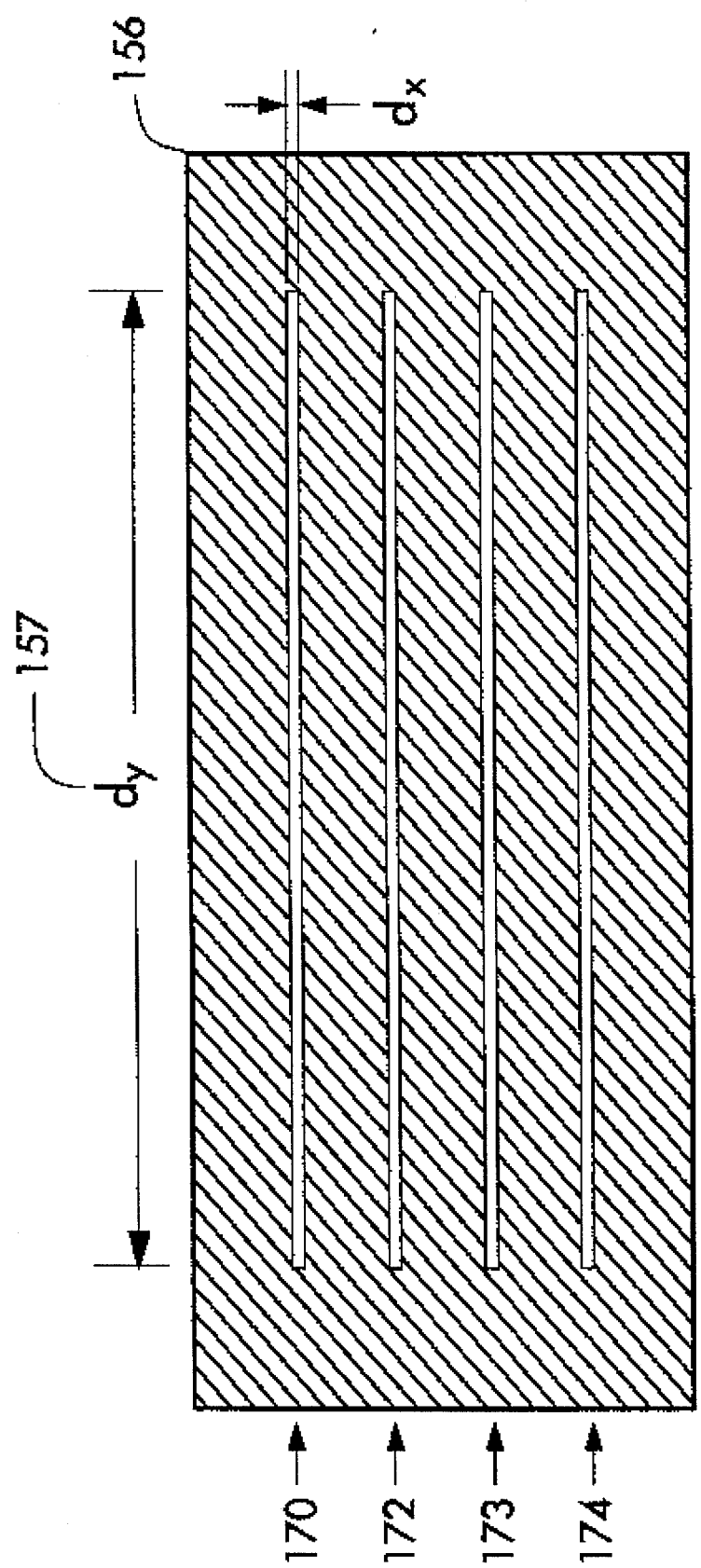
FIG. 10 is a detailed view of a mask used in the optical imaging system of FIG. 8.

The detailed operation of each of the optical imaging units 130 and 132 is best understood by reference to FIGS. 9 and 10. Referring to FIG. 9, there is shown a more detailed view of the optical imaging system 129 illustrating the operation of one imaging unit 130, it being understood that unit 132 functions in like manner. The optical unit 130 is configured to simultaneously view four stripes 150 across the right side of web 134 that are labeled 1–4 on FIGS. 8 and 9. In the preferred embodiment, each of the stripes 150 has a width of 0.5 millimeters and extends in a traverse direction perpendicularly across the web 134 for a distance of approximately 0.510 meters. Since two optical imaging units 130 and 132 are used to view the entire web, the stripes 150 may be thought of as actually extending continuously across the web. The four stripes 150 numbered 1–4 are separated each from the other by a distance of 4.0 millimeters in a direction parallel to the direction in which the web 134 moves. The spacing, edge to edge, between the four stripes 150 is 3.5 millimeters.

The optical imaging system 129 includes a pair of lenses 152 and 154 and a spatial mask 156 as seen in FIG. 9. The purpose of the lenses 152 and 154 is to image the web 134 in or near the object plane onto a CCD array 184 in camera 130 after reflection from the front surface of mirror 160 and passage through or reflection from a spectrally dispersive element 159. The function of the spatial mask 156 is to restrict the view of the CCD and grating assembly 159 to the four stripes 150. The function of the dispersive element 159, which may be either transmissive or reflective gratings, will be explained below. Since the web 134 is moving in the direction indicated by arrow 160, it will be appreciated that the CCD 184 is viewing entities in the web four separate times, corresponding to four different object/image points. That is, each entity in 100% of the web 134 will pass through each of the four stripes 150. Therefore, entities in that portion of the web 134 that is first viewed in the first of the stripes 150 will be viewed a second time in the second stripe 150, a third time in the third stripe 150, and a fourth time in the fourth stripe 150. As described in greater detail hereinafter, this redundancy is provided for the purposes of increasing the amount of information obtained and, thereby, increasing accuracy and precision.

In FIG. 9, only the central rays 152-1, -2, -3, -4 and central spectral component are shown prior to incidence upon the spectrally dispersive element 159, for clarity. Spectral dispersion 153 illustrated in FIG. 9 is for 8 components.

The signals from the CCD 184 are transmitted to readout electronics 162 which are a part of the acquisition and control unit 140. The readout electronics 162 provide an output to an image processor 164 whose output is applied to a display and storage unit 166, both of which are part of the image processing and storage computer system 144.

The speed of the web 134 is constantly monitored by a speed detector, such as a rotary encoder 168, that provides speed information through readout electronics 162 to the computer system 144. This speed information is important so that the system can take advantage of the redundancy provided by the four stripes 150 and so that undesired entities, such as neps and trash, detected by the assembly 129 may be tracked as to position in the web and excluded downstream.

Referring now to FIG. 10, a detailed view of the mask 156 is shown. The mask 156 includes slits 170, 172, 173, and 174 that restrict the image regions of the CCD 184 and grating assembly 159 to the four stripes 150 in the object space. Thus, the slits 170, 172, 173, and 174 control the size and shape of the stripes 150. Since it is desired to provide stripes having a width of 0.5 millimeters, the width ($d_x$) is determined by the product of the desired width in object plane, 0.5 millimeters, and the magnification of the first optical element 152. The width of the mask $d_y$ (157) is determined by the product of the magnification of the lens 152 and the width of the web that is desired to be inspected $Y_0$ (131), approximately 0.51 meters including 0.01 m overlap. For an optical element 152 with a focal length of 60 millimeters located 1 meter away from the web:

$$M = 63.8 \cdot 10^{-3}$$

$$d_x = 31 \text{ µm and}$$

$$d_y = 32 \text{ mm.}$$

The mask 156 can be constructed of precision cut metal film, or a chrome ruling on a glass substrate, or by photolithography means.

A reflective grating 159 is illustrated in FIG. 9 which is preferable for visible and near infrared radiation. Light enters the assembly 130, passes through mask 156 to the spectrally dispersive grating 159, then through an electronic shutter 175 controlled by computer system 144, and finally impinges upon a CCD array 184. The diffraction grating 159 disperses the incoming light into eight spectral channels, and the grating is oriented so that dispersion occurs in a direction corresponding to and parallel with the movement direction of the web 134. The dispersion occurs in a direction perpendicular to the longer axis of slits 170, 172, 173 and 174 and perpendicular to the four stripes 150. The diffraction grating is designed and dimensioned so that it spreads the eight spectral components over an area of the CCD corresponding to 4 millimeters on the web. Thus, instead of forming one image of each of the stripes 150 on the array 184, the system focusses eight side-by-side spectrally different images of each of the stripes 150 on the array 184. It will now be appreciated that the size of the four stripes 150 and the spacing between the stripes 150 was chosen to allow for eight images of each stripe on the CCD array 184 without allowing any overlap. Since the diffraction grating separates the light into spectral channels, each of the stripe images formed on the array 184 will provide different spectral information for each of the stripes 150. This design leads to a simple, compact design for observing spectral information in the visible and near infrared wavelengths using a CCD array 184 that measures only the intensity of the light striking it.

When it is desired to sense radiation outside the visible region, the diffraction grating 159 is preferred. If only visible or very near infrared radiation is sensed ($\lambda < 1.2$ µm), the reflective grating 159 can be replaced with a transmission grating. For near infrared radiation, the CCD array 184 must be of the type sensitive to the non-visible light being used. For example, for near infrared radiation up to $\lambda \approx 3$ µm, the CCD array may be a platinum silicide or mercury cadmium telluride array. For these applications, however, the arrays typically provide lower resolution than arrays in the visible range. Suitable near infrared radiation CCDs are manufactured by EGG of Massachusetts.

In the above description, particularly with reference to FIG. 9, optical imaging unit 130 has been described along with the acquisition and control unit 140. It will be appreciated that the units 132 and 142 are substantially identical to units 130 and 140, respectively, and FIG. 9 will be understood to describe and represent both imaging units 130 and 132 and both acquisition and control units 140 and 142. FIG. 9 will be further understood to describe the laboratory instrument or on-line monitoring instrument embodiments of FIGS. 1–5 and FIG. 7 or embodiments which examine fiber entities. The described embodiments are not limited to undesirable entities such as neps (including seed coat fragments) or trash.

Figure 11:
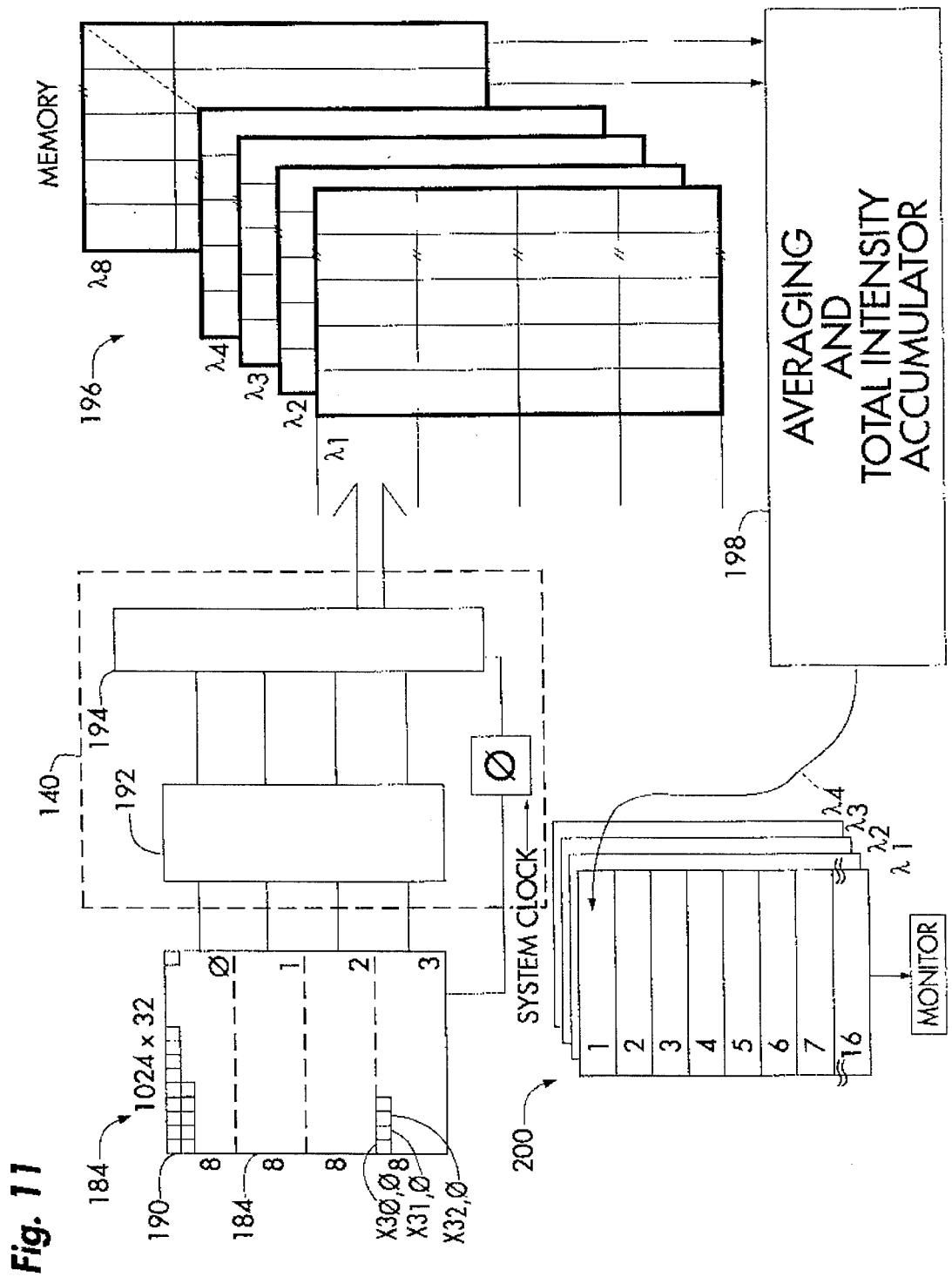
FIG. 11 is a schematic diagram illustrating how the CCD camera is read into memory and into an image buffer.
Figure 12:
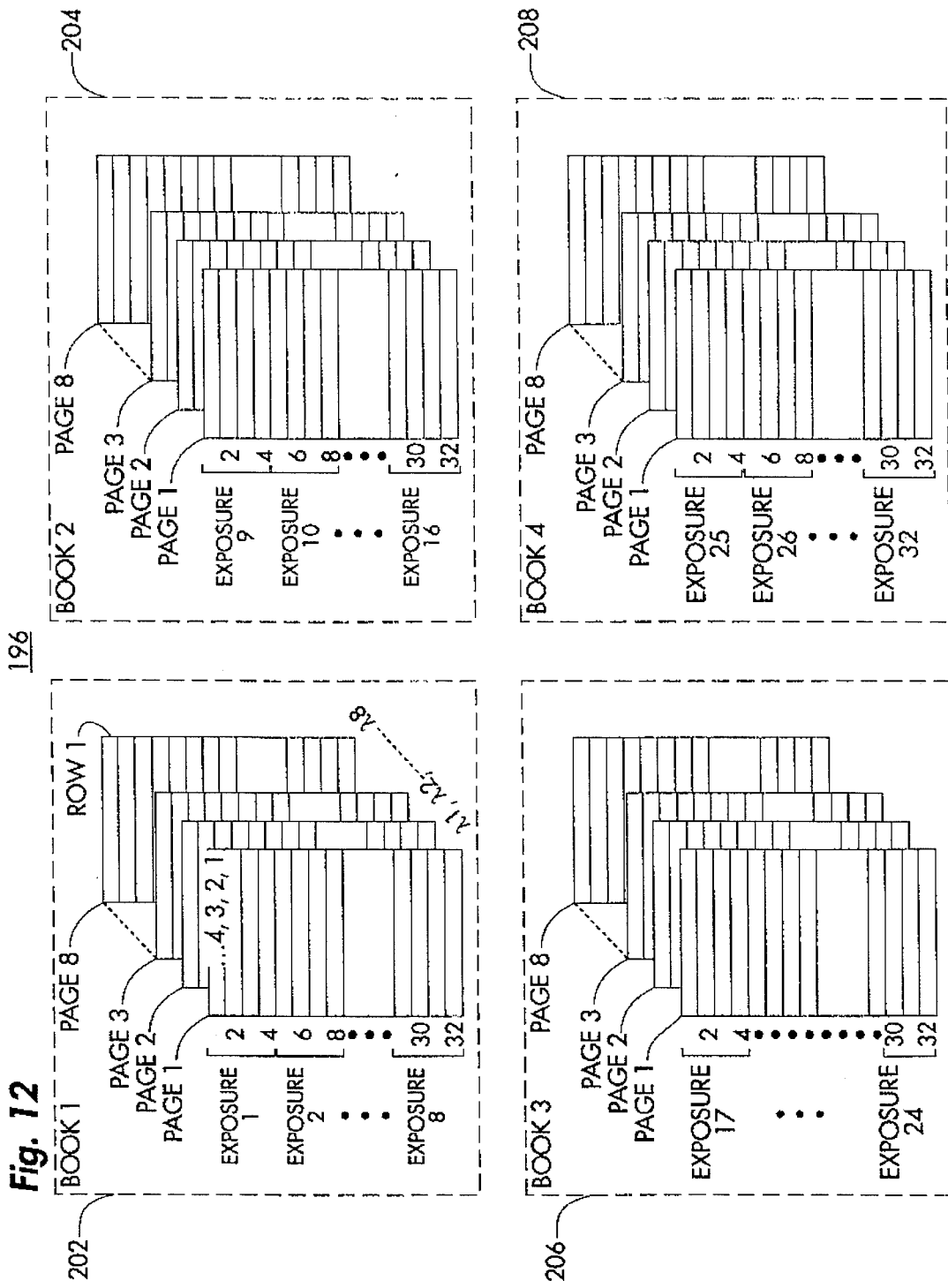
FIG. 12 illustrates four books of memory into which images from the CCD are stored.
Figure 13:
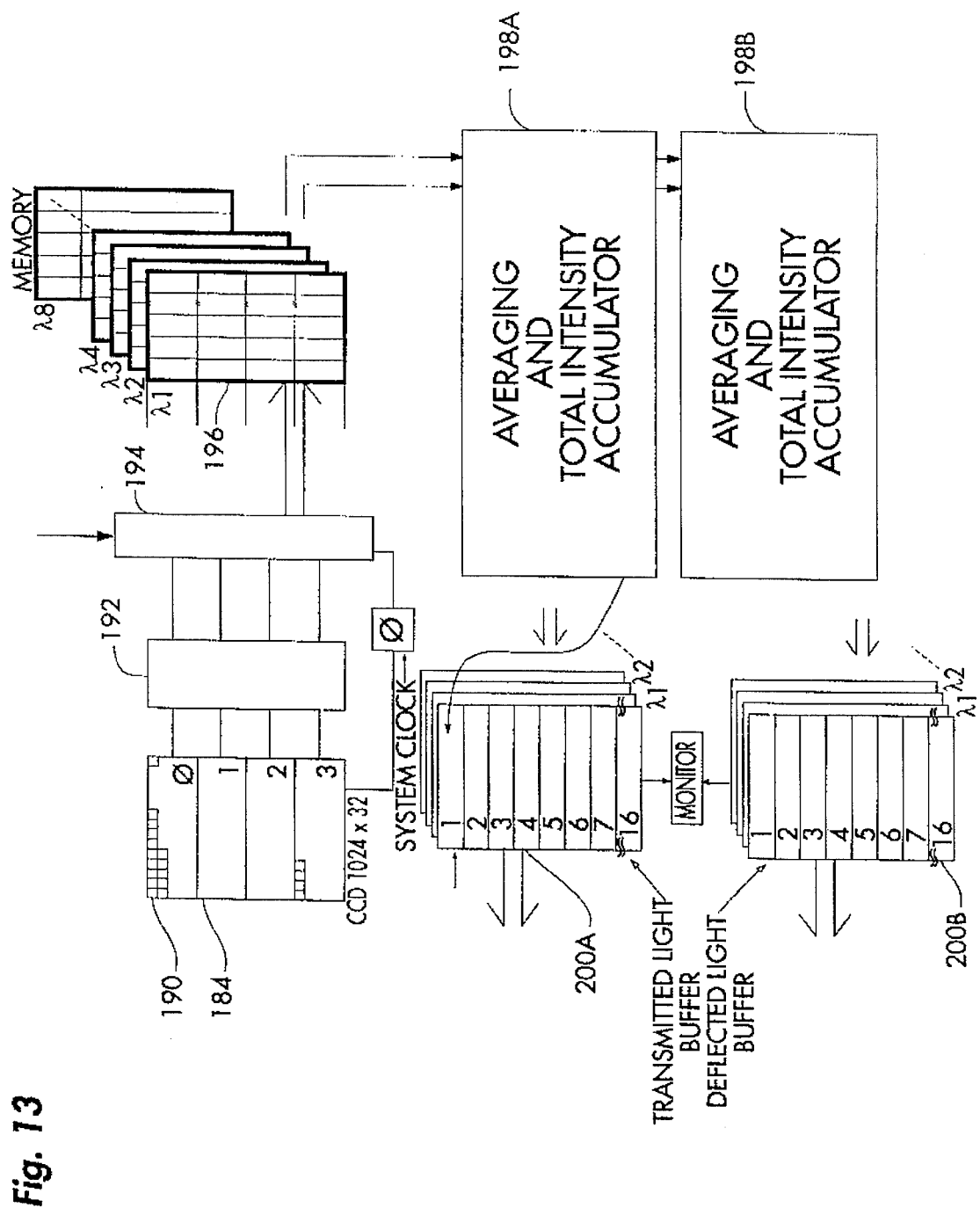
FIG. 13 illustrates an alternate system for reading the CCD camera and storing images in memory.

Signal processing aspects of the system 129 shown in FIG. 9 may be better understood by reference to the electronic and digital processing elements illustrated in FIGS. 11–13. The CCD array 184 consists of 1024 by 32 image pixels 190 arranged so that the 1024 pixel row is oriented parallel to the stripes 150 or perpendicular to movement of the image of web 134 on the array 184. Radiation falling on each pixel produces a charge which is transferred to the CCD terminals and converted to a voltage signal. The pixel voltages of array 184 are preferably read four pixels at a time by an A/D convertor. The voltage sensed by each pixel 190 is converted to a digital number by A/D 192 which is output through the DEMUX 194 to digital memory 196. The memory is read by an averaging and total intensity accumulator 198 and its output is applied to an image buffer 200. The function of the accumulator 198 is to average four time-separated rows of 1024 pixel output from the array 184 to produce each row of the image signal placed in the image buffer 200. The averaging process may best be understood by again referencing FIGS. 8 and 9 and considering a single one-half millimeter segment of the web 134 as it passes across the stripes 150. Consider first that this segment first appears in the first stripe 150. The electronic shutter 175 exposes the CCD 184 and this segment of the web will be viewed for the first time. The segment will then move from the first stripe 150 to the second stripe 150. The image processor 144 receives speed information from the encoder 168 and causes the shutter 175 to open each time the web moves one-half millimeter. Thus, the segment will be positioned in the second stripe 150 when the shutter 175 opens for the ninth time and the segment will be viewed for a second time by the CCD array 184. Likewise, on the seventeenth exposure of shutter 175, the segment will be in stripe 3; on the twenty-fifth exposure of shutter 175, the hypothetical segment will be in stripe 4 and, thus, it will be viewed for the third and fourth times. From the above explanation, it will be appreciated that each segment of the web will have the same hypothetical journey as described above and will be viewed four times. Thus, by averaging the first, ninth, seventeenth and twenty-fifth viewing of each 0.5 mm segment, an average measurement for each segment is obtained. Before explaining the second, tenth, eighteenth, and twenty-sixth shutter openings, and so forth, so that the entire web is examined, we explain the memory architecture.

Referring now to FIG. 12, the locations and control of the memory 196 may be visualized. The memory 196 is divided into four books, books one through four, which are identified by characters 202, 204, 206 and 208. Referring to FIGS. 11 and 12, the acquisition and storage of data are explained as follows. Upon the receipt of a correct position indication from the rotary encoder 168 (FIG. 9), the shutter 175 (FIG. 9) opens for approximately 0.0001 second to expose the CCD array 184. The process of image acquisition begins by reading the first 1024 pixel line of the CCD array 184, four pixels at a time, and storing it in the rightmost 1024 locations of the first row of the first page of the first book. The next 1024 pixel line is read from the array 184 and is stored in book one, page two, row one, because it represents the same spatial information as the first line, but at a different spectral wavelength. Each book contains eight spectral pages and the first eight lines of the CCD array 184 are read into the first rows of the eight pages of book one. The next eight lines of the CCD array 184 are stored in the second row of the eight pages of book one. The next eight lines of the CCD array 184 (lines 16–24) are stored in row three of pages 1–8 of book one, and the final eight lines of the CCD array 184 are stored in row four of the eight pages of book one.

The CCD has now been fully read, it is cleared, and the processor 144 waits until the encoder 168 indicates that the web 134 has moved forward 0.5 millimeters. At that point, the shutter 175 will expose again and create exposure number two. Exposure number two is stored in book one, rows 5–8, of pages 1–8 in the manner described above. Likewise, subsequent exposures are stored in book one until exposure eight is stored in rows 29–32 of pages 1–8 of book one. On the ninth exposure, book two is begun as indicated by character 204 in FIG. 13. Book two will contain exposures 9–16. Likewise, books three and four are created for storing exposures 17–24 and exposures 25–32, respectively. From the above discussion it will be appreciated that book one contains the oldest exposures and book four contains the most recent exposures.

It will further be appreciated that row one of each of the eight pages in book one corresponds to the same web segment image as row two of each of the pages of book two, as row three of each of the pages of book three, and as row four of each of the pages of book four. Thus, to produce row one of the first page in the image buffer 200, the accumulator 198 averages book one page one row one+book two page one row two+book three page one row three+book four page one row four. The accumulator 198 produces row one of pages 2–8 in the image memory buffer from pages 2–8 of books 1–4 in the same manner as described above.

To produce row two of page one in the image buffer 200, the accumulator 198 uses data obtained from exposures 2, 10, 18, and 26. Row two of image buffer 200 is obtained by averaging book one page one row five+book two page one row six+book three page one row seven+book four page one row eight. Likewise, each succeeding exposure is used to create the first eight rows in the eight pages of the image buffer 200. As another example, to produce row eight of the image buffer 200, the accumulator 198 adds book one row twenty-nine+book two row thirty+book three row thirty-one+book four row thirty-two. After the eighth row of image buffer 200 has been calculated, books two, three and four are redesignated as books one, two and three, respectively. Then, a new book four is created using the next eight exposures from the CCD 184, and the next eight rows for each of the eight pages of the image buffer 200 are calculated in the same manner as the first eight rows were calculated. This process continues indefinitely so that the image buffer 200 is a scrolling image buffer and always contains sixteen rows of image information on all eight pages.

From the above description, it will be appreciated that the image buffer always contains eight images, which have been referred to as "pages," of sixteen rows each of the web 134. Each of the eight images (pages) differs from the other in image buffer 200 based on wavelength. That is, each image represents a particular spectral range. If the web is producing an image in that particular spectral range, then such image will appear on the page of image buffer 200 containing that particular spectral range.

The output of the image buffer 200 is further analyzed as described in greater detail hereafter following a description of an alternate embodiment shown in FIG. 13 in which the accumulator 198 has been divided into two accumulators 198a and 198b, and the image buffer 200 has been divided into two buffers 200A and 200B. It will be understood that FIG. 13 is symbolically representing these elements and it is not necessary to actually physically separate the accumulators or the image buffers, but it is helpful to the explanation of the operation to so separate them.

The embodiment shown in FIG. 13 illustrates another way to take advantage of the redundancy that is built into the system 129. It will be recalled that each segment of the web 134 is viewed or imaged four times by the CCD 184. In the embodiment described above, these four redundant images were averaged to produce a single image. However, in the embodiment shown in FIG. 13, the redundancy is used in a different way. To utilize this embodiment, the illumination of the web 134 is changed after every sixteen exposures. For example, during the first sixteen exposures, the light source 138 is turned on to illuminate the web 134 from the back side of the web so that only light which transmits through the web is received by the detector 184. On the second sixteen exposures (exposures 17–32) source 138 is turned off and source 140 is turned on so that only light reflected from the web is received by the array 184. Thereafter, the sources 138 and 140 are alternately turned on and off every sixteen exposures so that the web 134 is illuminated only from one side at a time. The accumulator 198a produces the image buffer 200A in book form in the manner described above, except that accumulator 198a receives data only from the first set of sixteen exposures plus every odd set of sixteen exposures thereafter when the source 138 is on. The accumulator 198B produces the image books in buffer 200B based only on even sets of sixteen exposures when source 140 is on and source 138 is off. Thus, image buffer 200A contains a transmitted light image and buffer 200B contains a reflected light image. Each of these images is actually eight images contained on eight separate pages in the manner described previously.

Another method for operating accumulators 198a and 198b is to change to the illumination after every eight exposures so that source 138 is on during exposures 1–8 and exposures 17–24, while source 140 is on during exposures 9–16 and 25–32. In such case, the accumulator 198 would produce information for the image buffer 200A only from odd numbered sets of eight exposures, and 198 would produce data for image buffer 200B only from even numbered sets of eight exposures.

Since there is a quadruple redundancy provided by the system shown in FIG. 8, if desired, all true redundancy may be eliminated and the web 134 may be observed under four different light conditions as it passes stripes 150. For example, the mat could be exposed to four different light conditions such that a different type of illumination is present each time a segment of the mat passes beneath one of the stripes 150. For example, the mat 134 could be illuminated with the color red for the first eight exposures, the color green for the second eight exposures, the color yellow for the third eight exposures and the color blue for the fourth eight exposures. On the fifth set of eight exposures, the light conditions would be cycled again in the same order as before for each set of eight exposures. In this manner, each segment of the mat 134 will be exposed to four different light conditions as it passes through stripes 150, and different portions of the mat 134 will be exposed to the various light conditions at differing locations. For example, one portion of the mat may be exposed to red at stripe one, whereas another portion of the mat will be exposed to red at stripe two. However, all segments of the mat will be exposed to all four light conditions, just at different positions. In this embodiment, it would be preferred to use four accumulators, such as accumulators 198a and 198b, each accumulator being programmed to accept data only when a certain light condition is illuminating the mat 134. In such case, each accumulator would be responsive to data from every fourth set of eight exposures.

By the examples given above, it is meant to illustrate that the optical system of FIG. 9 can be constructed with a desired amount of redundancy by changing the number of stripes 150. This redundancy can be used to reduce possible error by exposing the mat 134 identically as the mat passes under each of the stripes 150 and then averaging the results. Or one may use the redundancy to expose the mat to differing light conditions, such as different wavelengths or directions or type of light, and thereby acquire more information about the web 134.

Referring again to FIGS. 11 and 13, it will be recalled that the array 184 includes lines of 1024 pixels and each pixel observes a 0.5 mm×0.5 mm area of the web 134. Since the overall width of the web 134 is 1 meter, the two optical imaging units 130 and 132 may be set to overlap anywhere from 0 to 24 pixels. In the preferred embodiment, the units 130 and 132 are set to overlap by 20 pixels or 10 mm and, thus, each camera also has a viewing angle that overhangs the web on the outer edges by a distance of 4 pixels or 2 millimeters. The overlapping regions of the optical imaging units 130 and 132 are used to align the units 130 and 132 so that they are viewing precisely the same portion of the web 134 in the overlap region. After alignment, signals are appropriately treated in software to avoid double-counting. Thus, the overlap insures full viewing of the web 134 and it facilitates alignment of the units 130 and 132.

Identification of Entities

Figure 14:
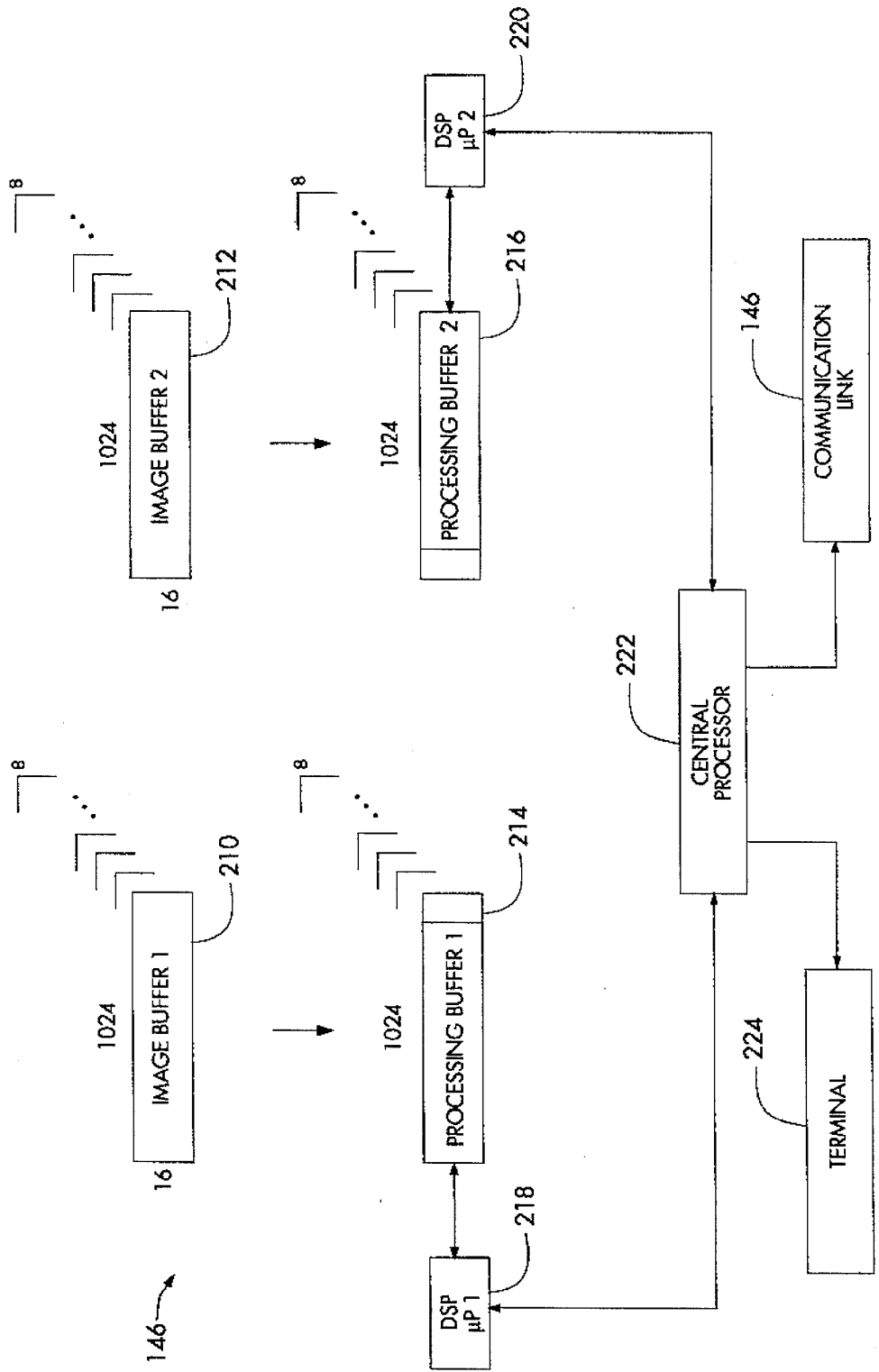
FIG. 14 is an overall block diagram of the processing system used to process the images produced by the optical imaging system.

Referring now to FIG. 14 a block diagram of the image processing and storage system 146 is shown. In this figure, two image buffers 210 and 212 are shown and each of these buffers is identical to buffer 200 shown in FIG. 11. Thus, the buffers 210 and 212 each contain eight images in eight memory locations which may be regarded as pages. Each of the pages is a 16 by 1024 array of data. The data of the image buffers 210 and 212 are read into processing buffers 214 and 216, respectively. Two digital signal processors (DSP) 218 and 220 are provided for operating upon the data in buffers 214 and 216, and each of the two DSPs 218 and 220 is under the control of a central processor 222. The processor 222 is also connected to a conventional terminal 224 and to a communication link 146.

Figure 17B:
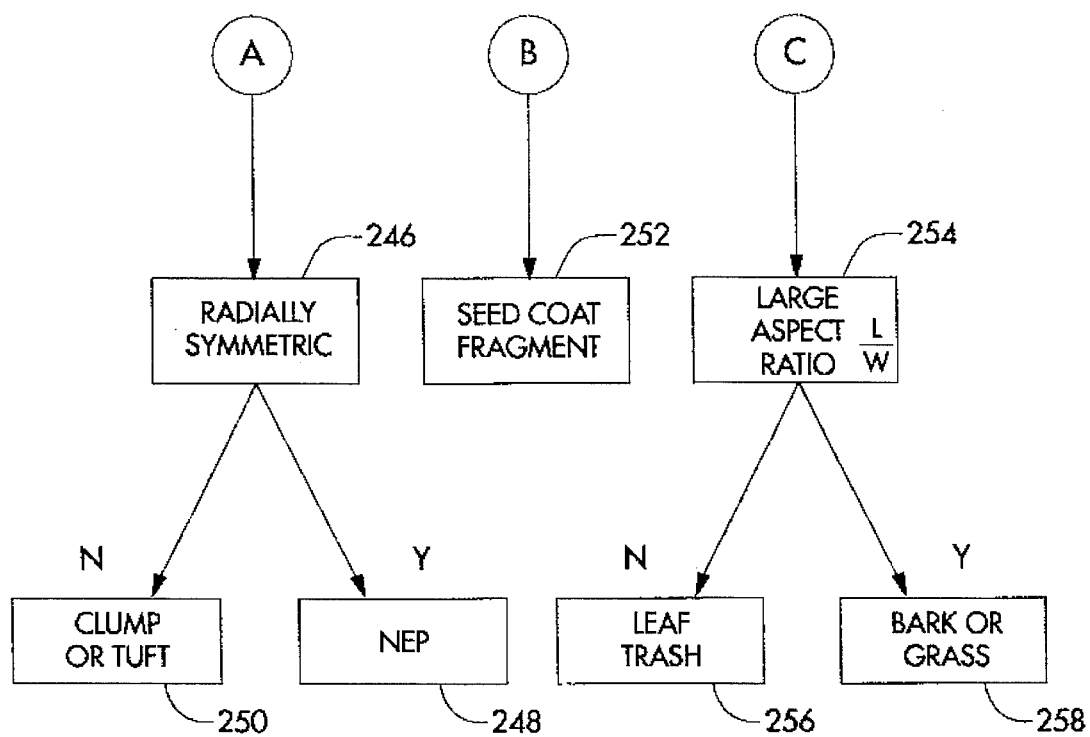

The raw data stored in the processing buffers 214 and 216 represents a multiplicity of features of the web 134. The DSPs 218 and 220 and the central processor 222 are programmed to use the spectral and spatial information contained in the images to locate entities of interest and classify or identify them. For example, in the preferred embodiment, the system 146 is programmed to locate trash and neps in a web of fiber 134. Referring to FIG. 17A, the first step 230 in the program is to assign each pixel in the processing buffers 214 and 216 a binary value, 1 or 0, depending on its intensity value. For present purposes, we define any pixel having a value 1 (on) to be a feature, and any pixel with a value of 0 (off) to be background. For image information that was received in the transmitted light mode, objects of interest attenuate light so the program assigns a value of 1 to any pixel that is less than 50% of the background values for all of the pixels. For image information that was obtained in the reflective light mode, we are interested in pixels that have a value that is 50% above the background value and they are assigned a value of 1 and the remaining pixels are assigned a value of 0. This assignment of a binary value is performed for all of the images in the eight pages of the buffers 214 and 216. By assigning the binary values in the manner described above, the same feature recognition techniques and sizing algorithms may be used to operate on images produced by either transmitted or reflected light.

Figure 15:
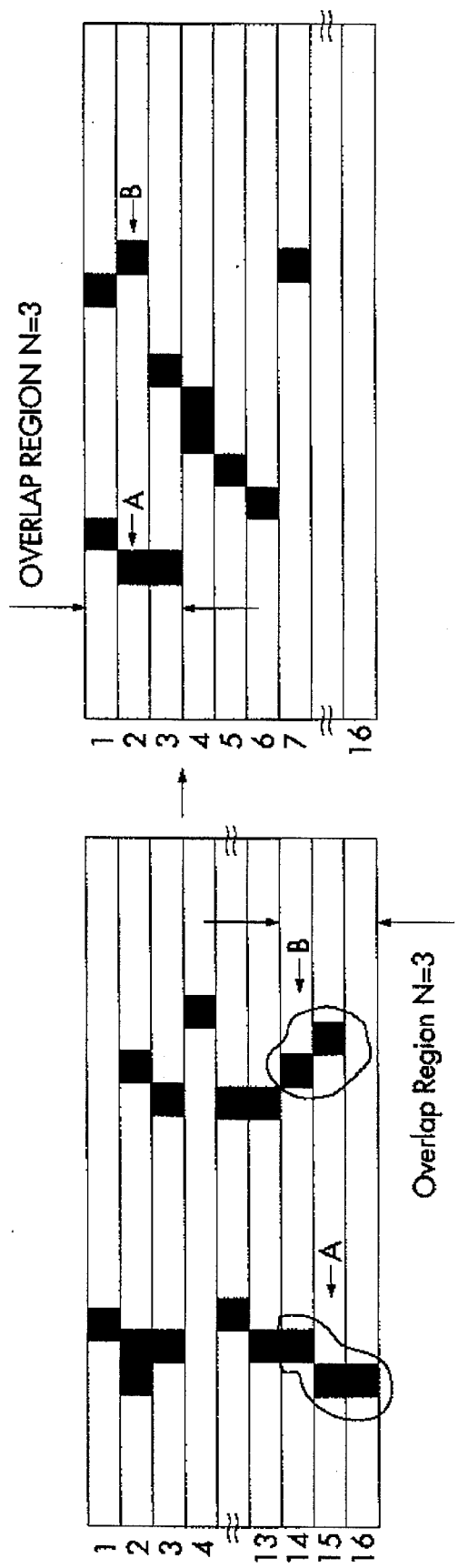
FIG. 15 is a graphical illustration of two images in the image buffer.

As indicated by step 232 in the flow chart following the conversion to a binary image, the processing buffer is screened by checking the upper pixel row for feature connections or overlapping shown graphically in FIG. 15. This can be accomplished by checking each pixel surrounding an upper row of pixels. If all five of the adjacent pixels are value 1, then the feature is considered to be an overlap. The number of rows occupied by that feature is then determined and that number is provided to the control circuitry to advance the refresh time by that number of rows. In this manner, the image buffer refresh time is controlled so that subsequent features provided to the processing buffers 214 and 216 do not overlap the edges. In an alternate embodiment, rather than control the refresh timing of the image buffers to avoid overlaps, the processor identifies features of interest that lie on the last row (trailing edge) of the buffers 214 and 216. These identified features on a boundary are saved in a separate memory. Then, when the processing buffers 214 and 216 are refreshed, the first row (leading edge) of each of the buffers 214 and 216 is analyzed to locate the remaining portion of the saved feature that overlapped the boundary between the two pages in buffers 214 and 216. In this manner, the DSPs 218 and 220 reconstruct a single feature (particle image) from two features that overlapped a boundary.

After overlaps have been identified and compensated for, features are identified at step 234. Features are defined as two or more adjacent pixels with a value of 1. Adjacency can be horizontal, vertical or diagonal, and the total size of the entity is calculated by counting all adjacent pixels. The boundaries of these features are then determined, such as by tracing techniques, high pass filtering or derivative calculations. Once the features have been located and the boundaries have been determined, the features are further identified as to shape. For example, shape is determined by approximating the boundary of a feature with a polygon using well known merging and splitting techniques. This technique works well because we expect relatively simple geometric shapes for most trash in cotton fibers and are primarily interested in the aspect ratio of the feature.

Figure 16C:
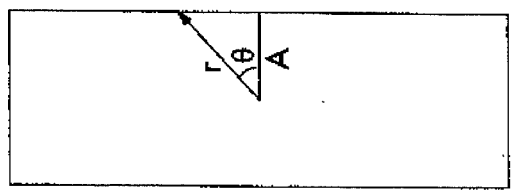
FIGS. 16A and 16C represent possible geometric shapes of entities and FIGS. 16B and 16D represent feature signatures of the entities shown in FIGS. 16A and 16C, respectively, where the signatures are generated by rotating a radius about the centroid of the geometric shape and graphing the length of the radius against its angular position.
Figure 16D:
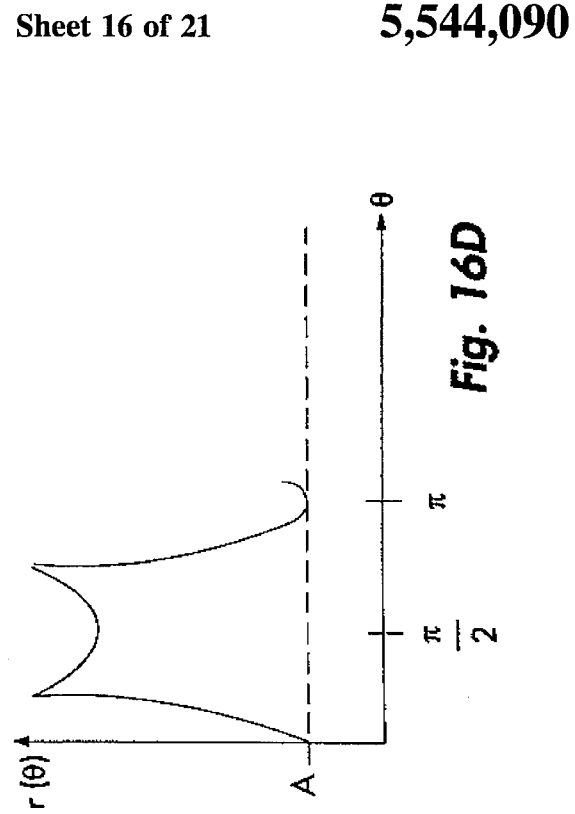
Figure 16A:
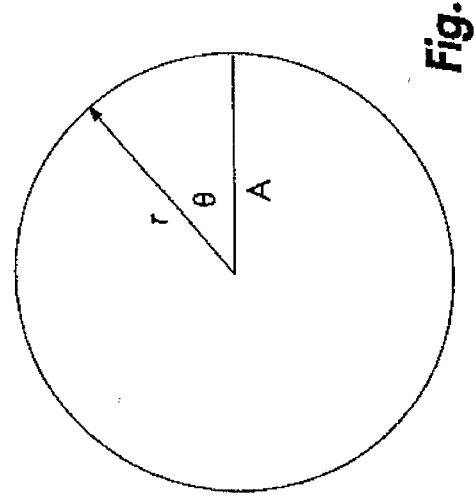

An alternate method for determining the shape of a feature is to define a one-dimensional signature of the particle boundary. In accordance with this method, the distance from the centroid of the feature to the boundary of the feature is recorded as a function of the angle of the centroid. In FIG. 16A, a circular feature is illustrated with its corresponding signature produced by rotating the radius about the centroid shown in FIG. 16B. Compare the signature shown in 16B to the signature produced by rotating a radius about the centroid of a rectangle such as shown in 16C to produce the signature shown in 16D. This method is particularly suited to recognizing particles with a high degree of radial symmetry. Another advantage of this approach is that the features can be represented in one dimension, thereby saving storage space and processing time.

After the features have been located and information has been obtained as to their size and shape, as indicated by step 236, the features are classified beginning with features with unusual spectral characteristics. Cotton color ranges from white to a very faint yellow in appearance, and any material which exhibits strong spectral responses other than yellow or white must be regarded as composed of foreign material for purposes of removal. For example, a nep containing sugar will exhibit a strong spectral response in the near infrared spectrum. Thus, any feature that has a strong response in the near infrared spectrum should be tagged as foreign material and removed as hereinafter described. The step 238 in the flow chart indicates immediate identification of foreign material based on spectral characteristics of a feature.

Figure 16B:
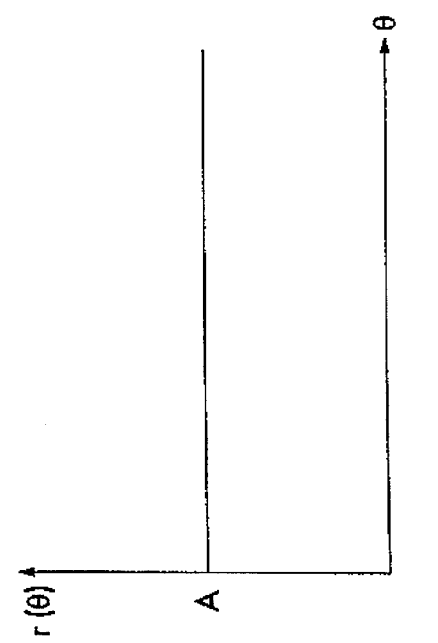

Next, features are selected one at a time from the reflected light buffer as indicated at step 239. If the feature is greater than 4 millimeters in diameter in any direction, for this particular application, it is regarded as an unknown foreign particle because most particles of interest such as trash, neps and seed coat fragments are smaller than 4 millimeters. Next, the size of the same feature, when illuminated with transmitted light, is measured and a ratio is calculated. That is, the size of the particle as observed in transmitted light is divided by the size of the particle as observed in reflected light. Since cotton is rather translucent, especially in a thin web, cotton itself is primarily observed by reflected light, as opposed to transmitted light. In contrast, opaque contaminants such as trash, grass and bark are revealed with high contrast under transmitted illumination, because they block substantially all of the light. Conversely, tight entanglements and clumps of fibers known as neps are best revealed in reflected light. Seed coat fragments which consist of both a translucent fiber mass and an opaque seed coat core are determined by comparing the response for both transmitted and reflected illumination. As shown in the flow chart at step 244, if the aforementioned ratio is less than 0.1, the feature is evaluated for radial symmetry at step 246. If the feature has radial symmetry, such as shown in FIGS. 16A and 16B, as indicated at step 248, it is identified as a nep. Otherwise it is identified as a clump or tuft as indicated at step 250. Referring to step 245, if the ratio falls between 0.1 and 0.8, it is immediately identified as a seed coat fragment as indicated at step 252. Finally, if the ratio is greater than 0.8 the program analyzes the aspect ratio as indicated at step 254. If the aspect ratio is small, such as less than 2, the particle is identified as leaf trash as indicated by step 256. On the other hand, if the aspect ratio is large, such as greater than 4, the trash is classified as bark or grass as indicated by step 258. The identification and classification of particles in the cotton web, such as the web 134 shown in FIG. 8, is useful for making decisions concerning the processing of the cotton both upstream and downstream from the point at which the cotton is observed. For example, if a very trashy cotton web is observed, the operator may choose to begin with cleaner cotton or increase the cleaning efficiency of upstream machines. If a particular type of trash is observed, it may indicate a particular type of problem upstream. For example, if odd color conditions are observed, it may indicate that a portion of a dyed rag has been introduced into the cotton upstream, and this event could ruin a great amount of end product.

Likewise, the identification and classification of particles in a cotton web provides useful information for downstream processing. For example, sticky neps, which would be indicated by a strong image in the near infrared region, interfere significantly with processing machinery and degrade the end product. Thus, in downstream processing, the elimination of the sugary neps could receive a high priority. In some applications, small leafy trash may present no problem, while bark fragments would be of concern. In such case, the downstream processing would emphasize the elimination of the detected grass and, perhaps, ignore the leafy trash.

Exclusion of Entities

Figure 19:
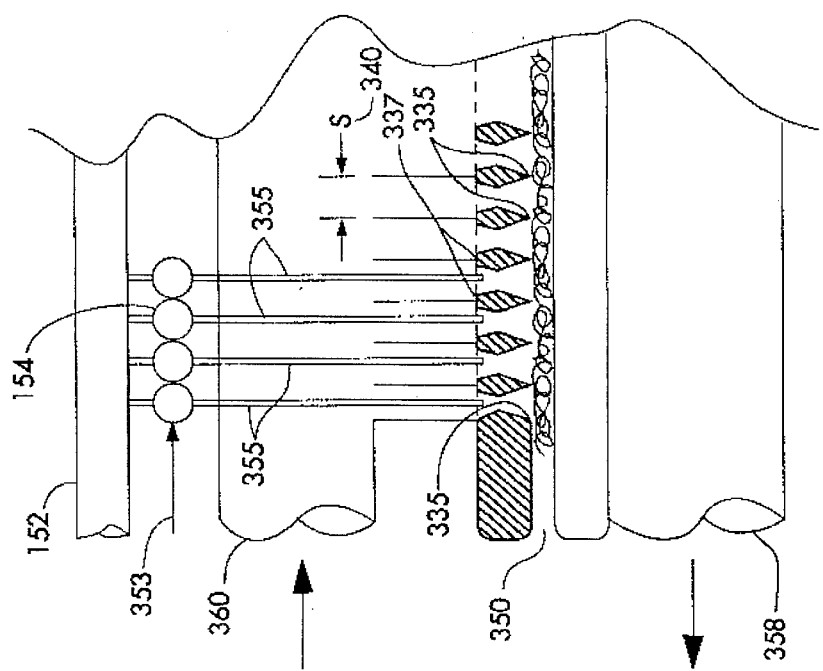
FIG. 19 shows a cross-sectional view of the excluder taken through section lines 19—19 shown in FIG. 18.
Figure 18:
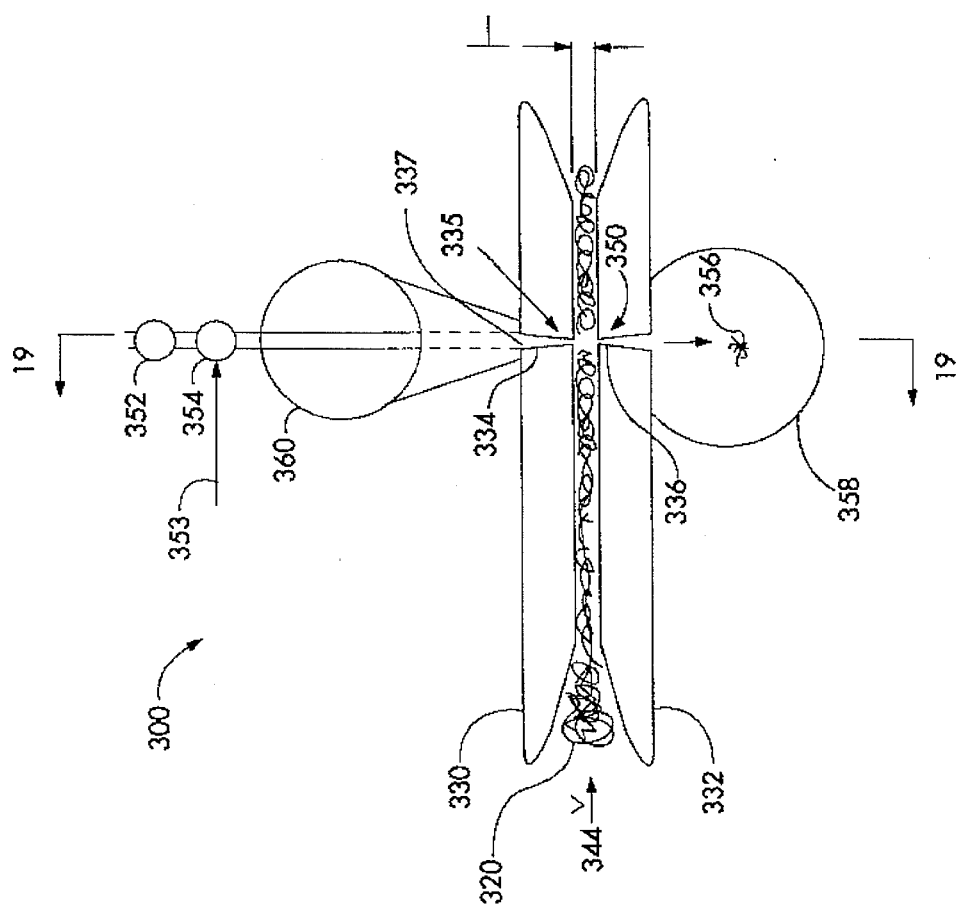
FIG. 18 shows an end cross-sectional view of a preferred excluder (ejector) of the present invention.
Figure 21:
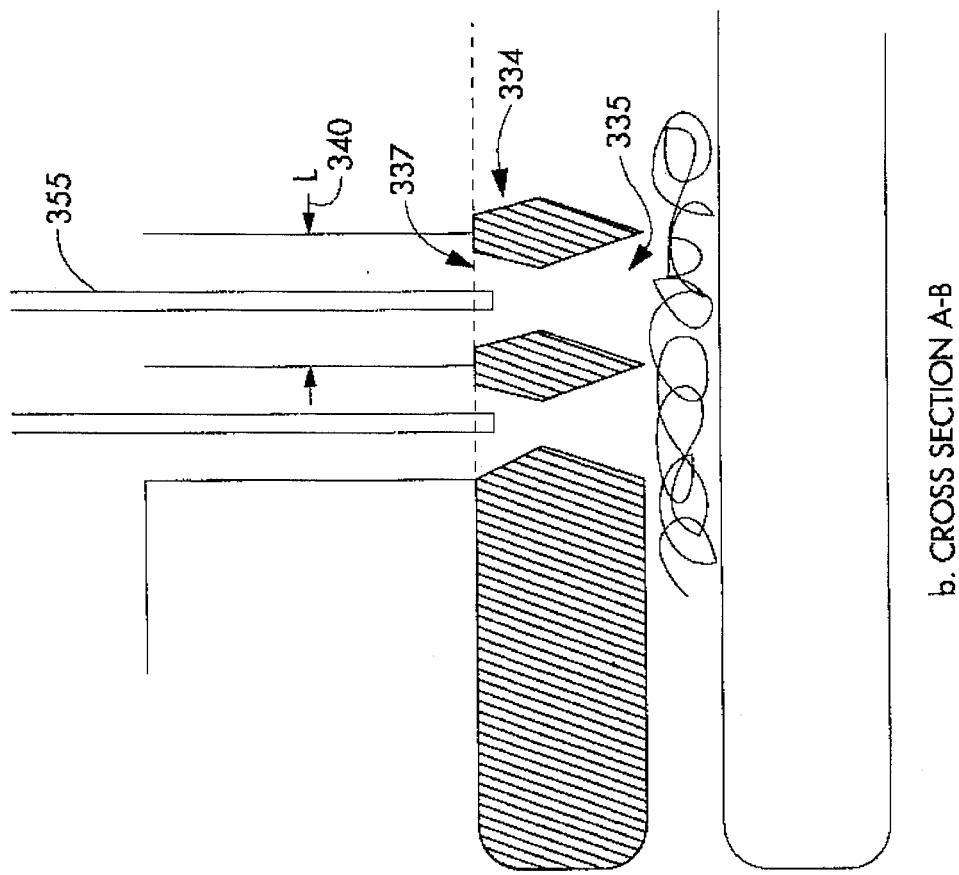
FIGS. 20 and 21 are enlarged views of the exclusions of 350 corresponding to FIGS. 18 and 19, respectively.
Figure 20:
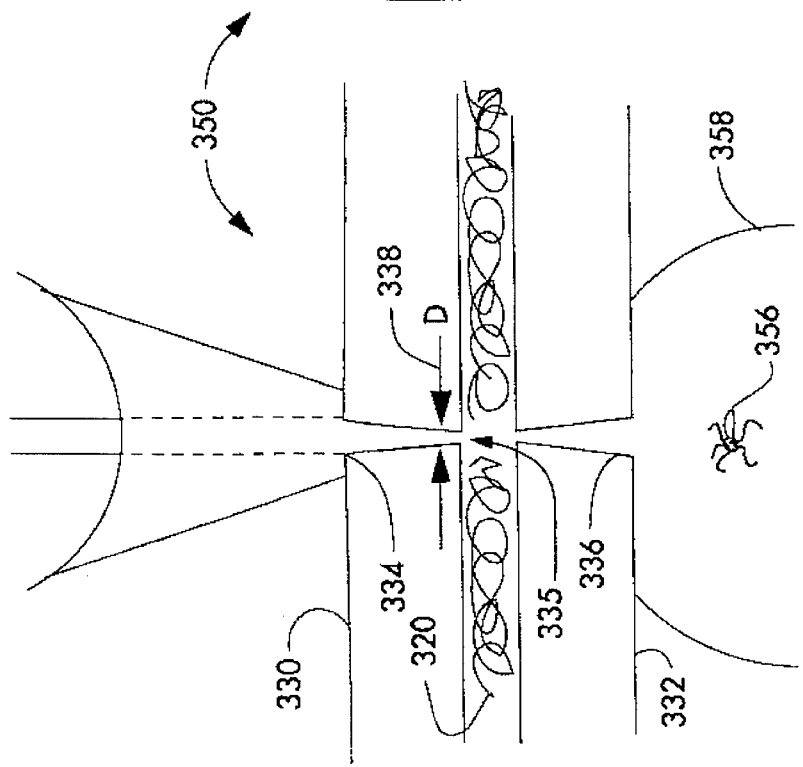

Having described the above apparatus and method for finding and identifying undesirable entities in a web of cotton or other fibers, excluding them from the web is now discussed. By means of the apparatus and method described above, entities are found and then identified in a prioritized classification as worthy of exclusion. FIG. 18 shows an end cross-sectional view of a preferred excluder 300 using compressed air to exclude or clear undesirable entities from the thin web 320, and FIG. 19 shows a cross-sectional view taken through section lines 19—19 shown in FIG. 18. FIGS. 20 and 21 are enlarged views of the exclusion zone 350 corresponding to FIGS. 18 and 19, respectively. In the views, FIGS. 18 and 20, the thin web 320 is seen to be transported through plates 330 and 332 which have a row of inlet nozzles 334 with approximately rectangular apertures 335 whose widths are on the order of three millimeters and are shown in FIG. 20 as having a width D, 338. In the cross-sectional view of FIG. 19, the length of the rectangular apertures 335 is shown to be on the order of one centimeter, and the spacing 340 (S) between the apertures is also in the order of one centimeter. The web 320 has a width of approximately one meter or 40 inches, and the row of nozzles 334 extends perpendicularly across the web 320. A single tapered deceleration nozzle 336 having a width also about three millimeters, which is shown in FIG. 18, and a length of a meter is positioned beneath the row of nozzles 334 and receives blasts of air therefrom.

Referring to FIGS. 8, 18 and 19, the row of nozzles 334 is positioned a known distance downstream of the stripes 150 shown in FIG. 8. Since the speed 344 of the web 320 is constantly reported to the computer system 144 by the rotary encoder 168, the computer 144 calculates the time required for any particular segment of the web to pass from, for example, the first one of the stripes 150 to the row of nozzles 334. When an undesirable entity is identified by system 144, its position (spatial coordinates) is determined with respect to the thin web 134 (320 in FIG. 18), and the system 144 calculates the time required for the undesirable entity to reach the row of nozzles. It will be recalled that the CCD arrays 184 in the imaging units 130 and 132 were arranged to view 0.5 mm stripes across the web 134 (320) with each pixel viewing a 0.5 mm rectangle. Thus, by counting pixels across the array to the image of the undesirable entity, the lateral position of the entity is determined. Based on the lateral position of the entity, the computer system 144 also determines which nozzle 334 will be above the entity when it arrives at the nozzles 334. At the appropriate time, when the entity arrives in the exclusion zone 350, a short burst of compressed air is applied to an appropriate one of a plurality of eductor feed pipes 355 by one of the fast acting solenoid valves 353. The computer system 144 applies control signals through control lines 353 to actuate one or more of the valves 354 and release compressed air through the feed pipes 355. Clean compressed air is supplied by pipe 352 to each of the feed pipes 355, land each of the feed pipes 355 is positioned in the mouth 337 of one of the nozzles 334. The compressed air exiting the feed pipe 355 entrains a volumetric flow from a plenum 360 that surrounds the nozzle mouths 337. The combined air flow from the feed pipes 355 and the plenum 360 forms a blast of air that strikes and ejects the entity 356 out of the thin web 320, through the decelerating nozzle 336, and into a waste pipe 358. The decelerating nozzle 336 is sized to cause a very slight positive initial pressure in the exclusion zone 350, thus pushing the surrounding components of the thin web 320 away from the exclusion zone 350 while at the same time blasting the undesired entity 356 into the waste collection pipe 358. After the initial positive pressure, when the compressed air from feed pipe 355 is turned off, there is a short interval of negative pressure caused by the momentum of the moving air in the decelerating nozzle 336 which causes the components surrounding the exclusion region (a rectangle of about 1 cm×3 mm) to move inwardly; this negative pressure interval is timed to partially close the exclusion hole in the web 320 but to not pull the web 320 into the waste collection pipe 358.

Air is continuously moving through waste collection pipe 358 to transport the undesirable entities out of the system. Waste collection pipe 358 and inlet plenum 360 are sized to not interfere with the independent operation of the exclusion nozzles 334 and 336, of which there are about one hundred for a web from a typical card. Furthermore, the supply air pipe 360 is sufficiently large that the interaction of the short pulse of any one of the exclusion nozzles 334 does not materially affect any of the others, even when more than one of these nozzles 334 is operating simultaneously. The air entering supply pipe 360 is filtered and otherwise conditioned to accommodate the purposes of exclusion.

Figure 22:
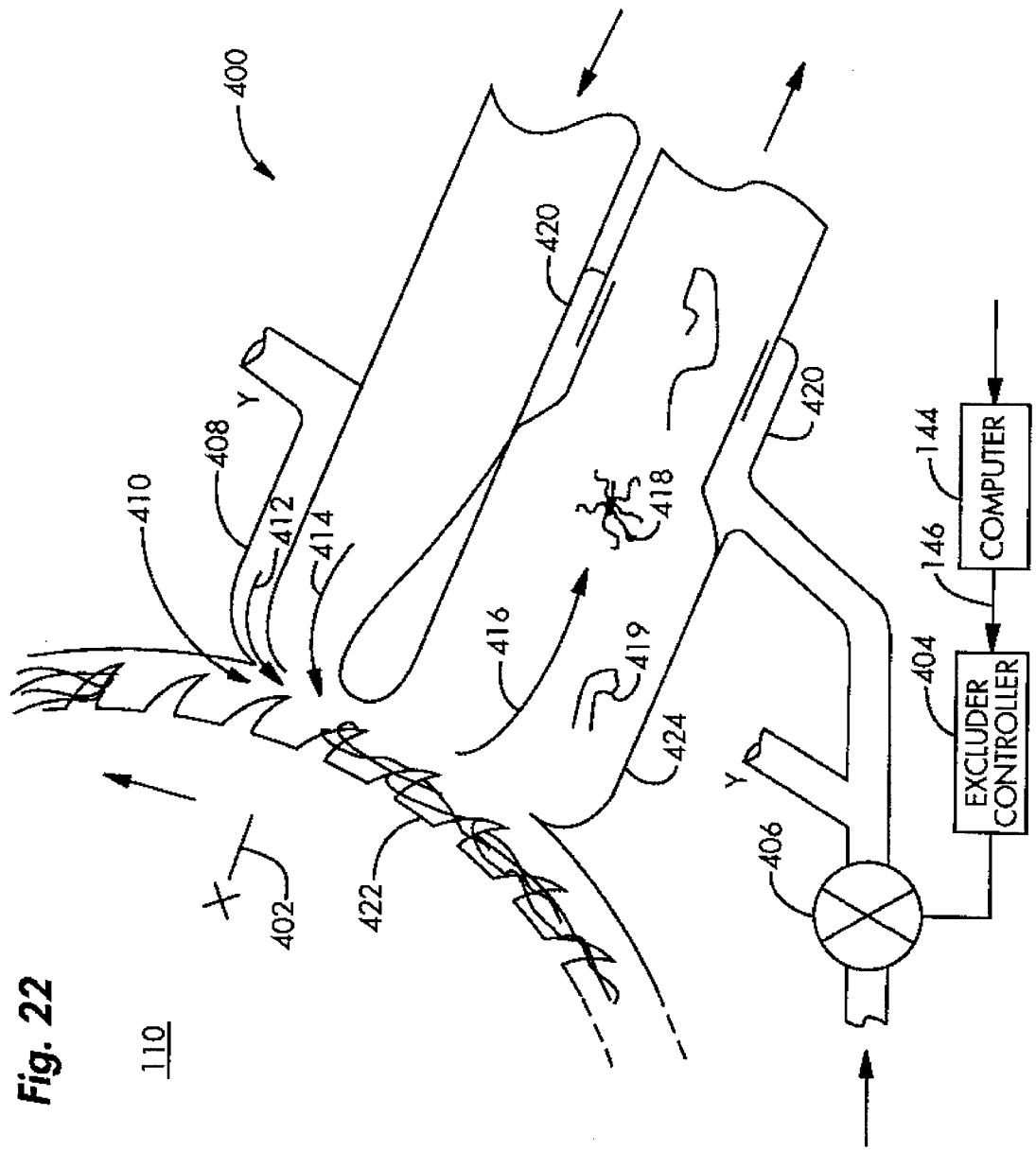
FIG. 22 is a cross-sectional view illustrating an ejector system of the present invention implemented in conjunction with a clothed cylinder such as a doffer cylinder.

FIG. 22 shows a second type of compressed air excluder 400 suitable for removing entitles from clothed cylinders, such as the doffer cylinder 110 of FIG. 6. A preferred location 402 for excluder 400 marked as "X" on FIGS. 6 and 22 is between the image analyzer system 50 and the crush rolls 122. Referring now to FIG. 22, the image analyzer system 50 Finds and Identifies an entity on the doffer cylinder 110 which is to be excluded, said pattern recognition, decisions and timing being handled by computer 144 in FIG. 8, and control signals on lines 146 which cause excluder controller 404 to energize fast-acting solenoid valve 406. This action supplies clean compressed air to plenum 408 and to blast air orifice 410. Simultaneously, (or separately, with another value and with different timing, if desired) solenoid valve 406 supplies clean compressed air to coaxial eductor 420. Assuming that blast air flow 412 and eductor driven air flow 416 start simultaneously, it is clear that the combined actions of pressure-driven blast air flow 412 and suction driven eductor air flow 416 are to "push and pull" a small volume or "pulse" of air, moving at high speed, across doffer wire 422 in a direction that permits the entity 418 and a few associated fibers 419 to be lifted off wire 422 and pulled into collector pipe 424. Flow 414 is driven by entrainment with flow 412 and by suction associated with flow 416. To summarize, the excluder 400 action may be thought of as providing a short duration (milliseconds) rapidly moving (near Mach 1) volumetric pulse (10's of cubic centimeters) which sweeps the entities off the cylinder wire and excludes them from the web. The width and length of the excluder orifices is about 3 mm×10 mm, like the excluder 300 of FIGS. 18–21, and there are also 100 of them across the one meter width of the web on the doffer cylinder 110.

Compressed air exclusion nozzles are illustrated in this preferred embodiment, but other exclusion means may be used as functionally equivalent. Such means include mechanical punching, cutting, or hooking, or the like. While it is preferred to use the system to Find and Identify the features of interest, such as trash in a moving cotton web, it should be understood that other detection systems could be used in conjunction with the excluder. Likewise, other excluders or fiber processors could be used with the detection system described herein. The various embodiments described herein are intended as examples illustrating the present invention and it will be understood that the present invention is capable of numerous rearrangements, modifications and substitution of parts without departing from the scope of the invention as defined in the appended claims.

What is claimed is:

1. An apparatus for monitoring and processing a web of textile materials while being processed in a textile mill, the web including a plurality of entities comprising:

means for monitoring the web of textile materials within a monitoring area and producing a monitor signal containing information corresponding to the content of the web, said information including the location of entities in the web;

computer processing means for receiving the monitor signal and determining the position of the entities based on the location information and for generating control signals based on the determined position; and web processing means positioned downstream of said monitoring area for receiving the control signals and for processing the web in response to and in accordance with the control signals for reducing the amount of entities contained in said web, there being a time delay between said monitoring and said processing.

2. The apparatus of claim 1 wherein said web processing means comprises:

ejectors positioned downstream of said monitoring area for selectively ejecting the entities from the web;

said computer processing means being operable to determine when one of more entities are positioned for being ejected by said ejector and issuing an eject command in response to the entities being so positioned; and said ejectors being responsive to the eject commands for ejecting the entities from the web.

3. The apparatus of claim 1 wherein said web processing means comprises:

a row of nozzles positioned in a side by side relationship downstream of said monitoring area and extending across the web for selectively ejecting the entities from the web;

said computer processing means being operable to determine when one of more entities are positioned adjacent said row of nozzles for being ejected by said nozzles and issuing an eject command in response to the entities being so positioned; and a source of pressurized air;

a plurality of fast acting pneumatic valves for receiving pressurized air from said source and selectively releasing said pressurized air for a limited time interval;

air transport means for transporting pressurized air released from said valves to said nozzles;

said valves including control means responsive to said eject commands for opening the valves and releasing a burst of air into said air transport means and into said nozzles when the entities are positioned adjacent to said nozzles; and said nozzles being positioned and oriented to direct pressurized air toward and into said web in response to said eject commands for ejecting entities from the web.

4. The apparatus of claim 1 wherein said web processing means comprises:

ejectors positioned downstream of said monitoring area for selectively ejecting the entities from the web;

said computer processing means being operable to determine when one of more entities are positioned for being ejected by said ejector and issuing an eject command in response to the entities being so positioned;

said ejectors being responsive to the eject commands for ejecting the entities from the web; and a receiver positioned to receive the entities ejected from the web and for producing a slight negative pressure in the web where the entity was removed for healing the web at the position where the entity was removed.

5. The apparatus of claim 1 wherein said web processing means comprises:

a row of nozzles positioned in a side by side relationship downstream of said monitoring area and extending across the web for selectively ejecting the entities from the web;

said computer processing means being operable to determine when one of more entities are positioned adjacent said row of nozzles for being ejected by said nozzles and issuing an eject command in response to the entities being so positioned; and a source of pressurized air;

a plurality of fast acting pneumatic valves for receiving pressurized air from said source and selectively releasing said pressurized air for a limited time interval;

air transport means for transporting pressurized air released from said valves to said nozzles;

said valves including control means responsive to said eject commands for opening the valves and releasing a burst of air into said air transport means and into said nozzles when the entities are positioned adjacent to said nozzles; and said nozzles being positioned and oriented to direct pressurized air toward and into said web in response to said eject commands for ejecting entities from the web;

said nozzles being dimensioned and configured with respect to the source of pressurized air and the web to produce a slight positive pressure in the region of the entity that is being removed so that the web is pushed out and separated by the initial burst of air from the nozzles;

a receiver positioned to receive pressurized air from the nozzles for receiving the entities ejected from the web, for initially providing a back pressure against the air pressure leaving the nozzles and creating an increased pressure in the region of the ejected entity for separating the web, and for producing a slight negative pressure in the web where the entity was removed for drawing together and healing the web at the position where the entity was removed.

6. An apparatus for monitoring and processing a moving web of textile materials while being processed in a textile mill, the web including a plurality of undesirable entities and moving at a speed in a direction generally parallel to the length of the web, comprising:

means for monitoring the web of textile materials within a monitoring area and producing a monitor signal containing information corresponding to the content of the web, said information including the location of undesirable entities in the web;

a speed detector for detecting the speed of the web and producing a speed signal in response to and indicating the web speed;

computer processing means for receiving the monitor signal and the speed signal and determining a position of the entities based on the location information and the speed of the web and for generating control signals based on the determined position;

web processing means positioned downstream of said monitoring area for receiving the control signals and for processing the web in response to and in accordance with the control signals for reducing the amount of entities contained in said web; and said computer processing means for determining the time at which one or more undesirable entities will be positioned at the web processing means based on the location information and the speed of the web.

7. The apparatus of claim 6 wherein said web processing means comprises:

ejectors positioned downstream of said monitoring area for selectively ejecting the entities from the web;

said computer processing means being operable to determine when one of more entities are positioned for being ejected by said ejector and issuing an eject command in response to the entities being so positioned; and said ejectors being responsive to the eject commands for ejecting the entities from the web.

8. The apparatus of claim 6 wherein said web processing means comprises:

a row of nozzles positioned in a side by side relationship downstream of said monitoring area and extending across the web for selectively ejecting the entities from the web;

said computer processing means being operable to determine when one of more entities are positioned adjacent said row of nozzles for being ejected by said nozzles and issuing an eject command in response to the entities being so positioned; and a source of pressurized air;

a plurality of fast acting pneumatic valves for receiving pressurized air from said source and selectively releasing said pressurized air for a limited time interval;

air transport means for transporting pressurized air released from said valves to said nozzles;

said valves including control means responsive to said eject commands for opening the valves and releasing a burst of air into said air transport means and into said nozzles when the entities are positioned adjacent to said nozzles; and said nozzles being positioned and oriented to direct pressurized air toward and into said web in response to said eject commands for ejecting entities from the web.

9. The apparatus of claim 8 wherein each of said nozzles comprises:

a feed pipe for receiving pressurized air from the source and delivering the air to a feed pipe end:

an eductor for receiving the feed pipe end and for supplying a second source of air, said eductor being configured and positioned with respect to said feed pipe end for supplying air from said second source and entraining the second source air in the pressurized air that escapes through the end of the feed pipe when said valves are actuated.

* * * * *